(12) United States Patent
Tsao et al.

(10) Patent No.: US 9,828,398 B2
(45) Date of Patent: Nov. 28, 2017

(54) COMPOUND FOR BONE SCANNING AND USE THEREOF

(71) Applicant: TAIWAN HOPAX CHEMS. MFG. CO., LTD., Kaohsiung (TW)

(72) Inventors: Ning Tsao, Kaohsiung (TW); Chih-Wei Hsu, Kaohsiung (TW)

(73) Assignee: TAIWAN HOPAX CHEMS. MFG. CO., LTD., Kaohsiung (TW)

( * ) Notice: Subject to any disclaimer, the term of this patent is extended or adjusted under 35 U.S.C. 154(b) by 3 days.

(21) Appl. No.: 15/133,292

(22) Filed: Apr. 20, 2016

(65) Prior Publication Data

US 2016/0304545 A1    Oct. 20, 2016

Related U.S. Application Data

(60) Provisional application No. 62/149,783, filed on Apr. 20, 2015.

(51) Int. Cl.
*C07C 315/00* (2006.01)
*C07F 9/6524* (2006.01)
*C07F 9/38* (2006.01)
*A61K 51/04* (2006.01)
*C07F 9/40* (2006.01)

(52) U.S. Cl.
CPC ........ *C07F 9/6524* (2013.01); *A61K 51/0489* (2013.01); *C07F 9/3873* (2013.01); *C07F 9/405* (2013.01)

(58) Field of Classification Search
CPC ... A61K 51/0489; C07F 9/3873; C07F 9/405; C07F 9/6524
See application file for complete search history.

*Primary Examiner* — Yevegeny Valenrod
*Assistant Examiner* — Blaine G Doletski
(74) *Attorney, Agent, or Firm* — Bacon & Thomas, PLLC

(57) ABSTRACT

The disclosure provides a compound comprising bisphosphonate functional group and chelating agent. The bisphosphonate functional group part has high affinity for bone tissue, and the chelating agent part has high affinity for metal tracer such as radioisotope. The disclosed compound could be rapidly adsorbed onto the bone surface, and could steady emit ionizing radiation. Therefore, the disclosed compound is suitable for bone scanning technology to find abnormalities in bone.

5 Claims, 34 Drawing Sheets

COMPOUND FOR BONE SCANNING AND USE THEREOF

BACKGROUND

Technical Field

The disclosure is related to a compound have good character of bone scanning; more particularly to a compound with bisphosphonate group and chelating agent.

Description of Related Art

A bone scan or bone scintigraphy is a scanning technology to find certain abnormalities in bone. It is primarily used to help diagnose a number of conditions relating to bones, including: in situ or metastatic carcinoma in bone, locating some sources of bone inflammation (e.g. bone pain such as lower back pain due to a fracture), the diagnosis of fractures that may not be visible in traditional X-ray images, and the detection of bone damage due to certain infections and other problems. Bone seeking agents or bone seekers such as radiolabeled bisphosphonates have been used as radiopharmaceuticals for bone scanning. Bisphosphonates are taken up by the skeleton and suppress osteoclast-mediated bone resorption, and a radioactive substance called tracer undergoes radioactive decay, resulting in the emission of gamma ray(s) and/or subatomic particles such as alpha or beta particles. Then a special camera takes pictures of the tracer in the bones.

However, bisphosphonates have fairly weak bonding with tracer. Therefore, they tend to degrade with time and release tracer as an impurity. Moreover, the uptake of traditional radiolabeled bisphosphonates in bone takes 2 to 4 h after injection. This necessary delay could be a disadvantage for clinical use, especially for children.

SUMMARY

The disclosure provides a compound having good character for bone scanning.

According to one embodiment, said compound has following formula:

  (1)

wherein Q is a chelator-based bone seeking agent; $R_1$ is bisphosphonate group; and n is 1, 2, 3, or 4.

Preferably, $R_1$ is methylene diphosphonate group, hydroxymethylene diphosphonate group, pamidronate group or a combination thereof.

Preferably, Q is diethylene triamine pentaacetic acid (DTPA), monoamine-monoamide (MAMA), tetraazacyclic or a combination thereof.

Preferably, the bond between Q and $R_1$ is a conjugated bond.

Preferably, the compound or Q is chelated with a metal.

Preferably, the metal is Tc-99m, Ga-67, Ga-68, In-111, Cu (61, 62, 64), Gd, Fe or a combination thereof.

Preferably, the compound is used in imaging technology for bone metastasis and/or osteoporosis.

Preferably, the imaging technology is CT, MRI, PET or SPECT.

According to another embodiment, said compound have the following formula (2):

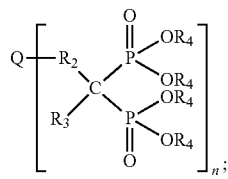

wherein Q is a chelator-based bone seeking agent containing nitrogen; wherein each $R_2$ is independently alkane or alkyl amine; wherein each $R_3$ is independently a hydroxyl group or hydrogen; and wherein each $R_4$ is independently hydrogen, an alkyl group or an aryl group.

According to another embodiment, said compound is one of the following formulas:

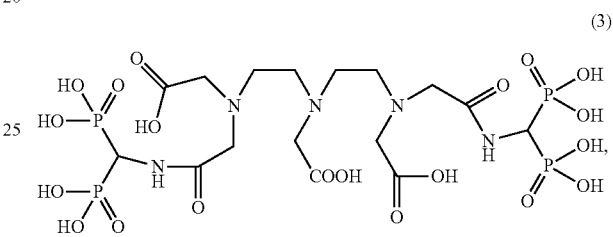  (3)

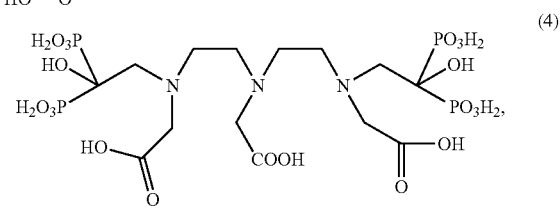  (4)

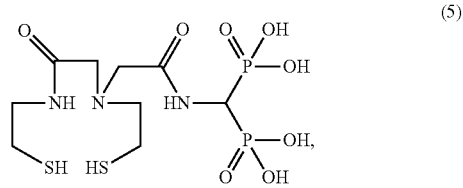  (5)

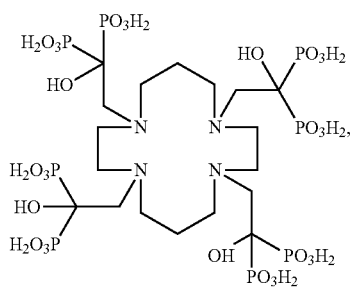  (6)

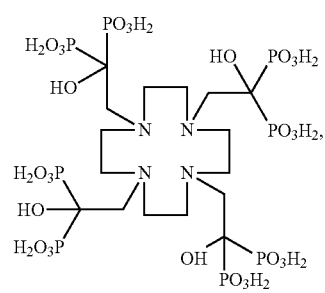  (7)

-continued

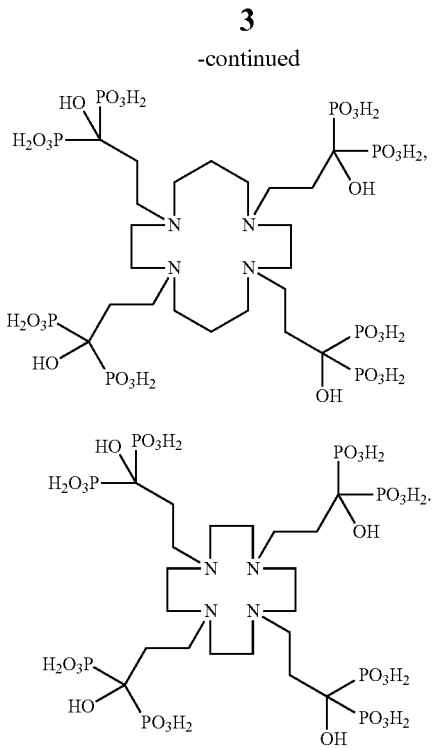

(8)

(9)

To sum up, the present disclosure provides a compound comprising a bisphosphonate functional group and a chelating agent. The bisphosphonate functional group moiety has high affinity for bone tissue, and the chelating agent moiety has high affinity for metal tracer such as radioisotope. That is, the present compound could be rapidly adsorbed to the bone tissue and could steady emit ionizing radiation (if chelating with tracer). Therefore, the present compound is suitable for bone scanning technology for purpose of finding abnormalities in bone.

Figure 1:
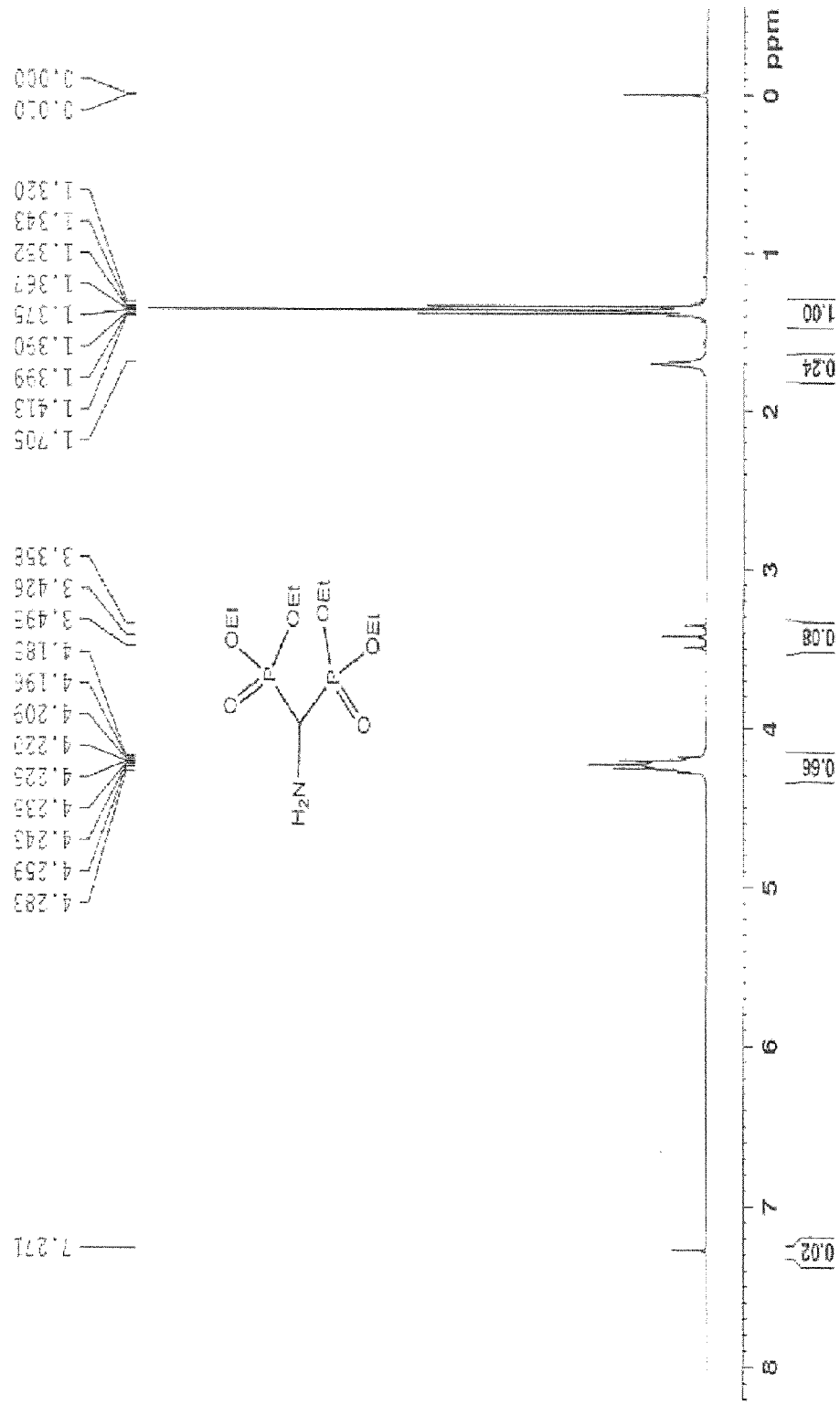
FIG. 1 shows $^1$H-NMR-spectra of AMDP-ester.

In the following detailed description, for purposes of explanation, numerous specific details are described in order to provide a thorough understanding of the disclosed embodiments. It will be apparent, however, that one or more embodiments may be practiced without these specific details. In other instances, well-known structures and process are schematically shown in order to simplify the drawing.

DETAILED DESCRIPTION

The following description will show the syntheses and uses of compounds according to the embodiments of present disclosure.

Example 1. Synthesis of Tetraethyl(Aminomethylene)Diphosphonate (AMDP Ester) and Bromoacetyl-AMDP-Ester The three-step synthesis method of AMDP ester and bromoacetyl-AMDP-ester is shown in Scheme 1.

Scheme 1: General Synthesis of AMDP ester and Bromoacetyl-AMDP-ester

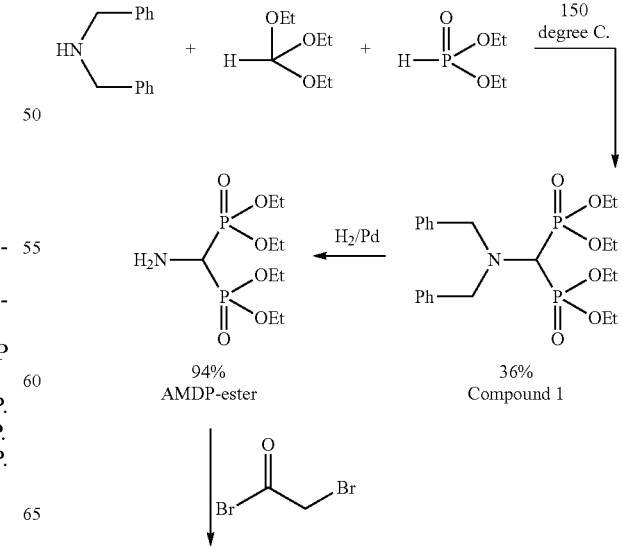

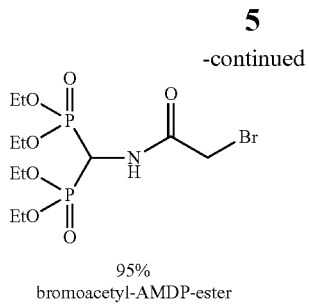

95%
bromoacetyl-AMDP-ester

Step a: Synthesis of Tetraethyl(N,N-dibenzyl)aminomethyl-bis(phosphonate) [Compound 1]

7.95 g (53.6 mmol) of triethylorthoformate, 19.19 g (138.9 mmol) of diethylphosphite and 8.84 g (44.8 mmol) of dibenzylamine were mixed together, and the resulting solution was refluxed for 5 hours under nitrogen atmosphere. The reaction mixture was then purged with nitrogen and heated at 150° C. for 20 hours. The reaction mixture was cooled and was added in 100 ml methylene chloride. The organic layer was washed with brine followed by 25% NaOH (25 ml, three times), and then dried over magnesium sulfate. After solvent evaporation, the residue was purified by silica gel column chromatography (ethyl acetate:hexane:methanol 14:5:1) to obtain 7.8 g of compound 1.

Step b: Deprotection of dibenzyl group from tetraethyl(N,N-dibenzyl)aminomethyl-bisphosphonate [Compound 1] to form AMDP ester 2.54 g (5.25 mmol) of Compound 1 was dissolved in 75 ml of anhydrous ethanol, then 1.0 g of palladium in charcoal was added. The solution was purged with hydrogen and then refluxed for 22 hours under hydrogen atmosphere. The reaction mixture was filtered through celite and the solvent was evaporated to obtain 1.54 g of product (AMDP-ester). FIG. 1 showed the correct proton NMR spectra of AMDP-ester (δ 7.2, singlet; δ 4.1-4.3, nonet; δ 3.3-3.5, triplet; δ 1.7, singlet; δ1.3-1.4, octet).

Step c. Synthesis of Tetraethyl (N-bromoacetyl)aminomethyl-bis(phosphonate) [bromoacetyl-AMDP-ester]

Figure 2:
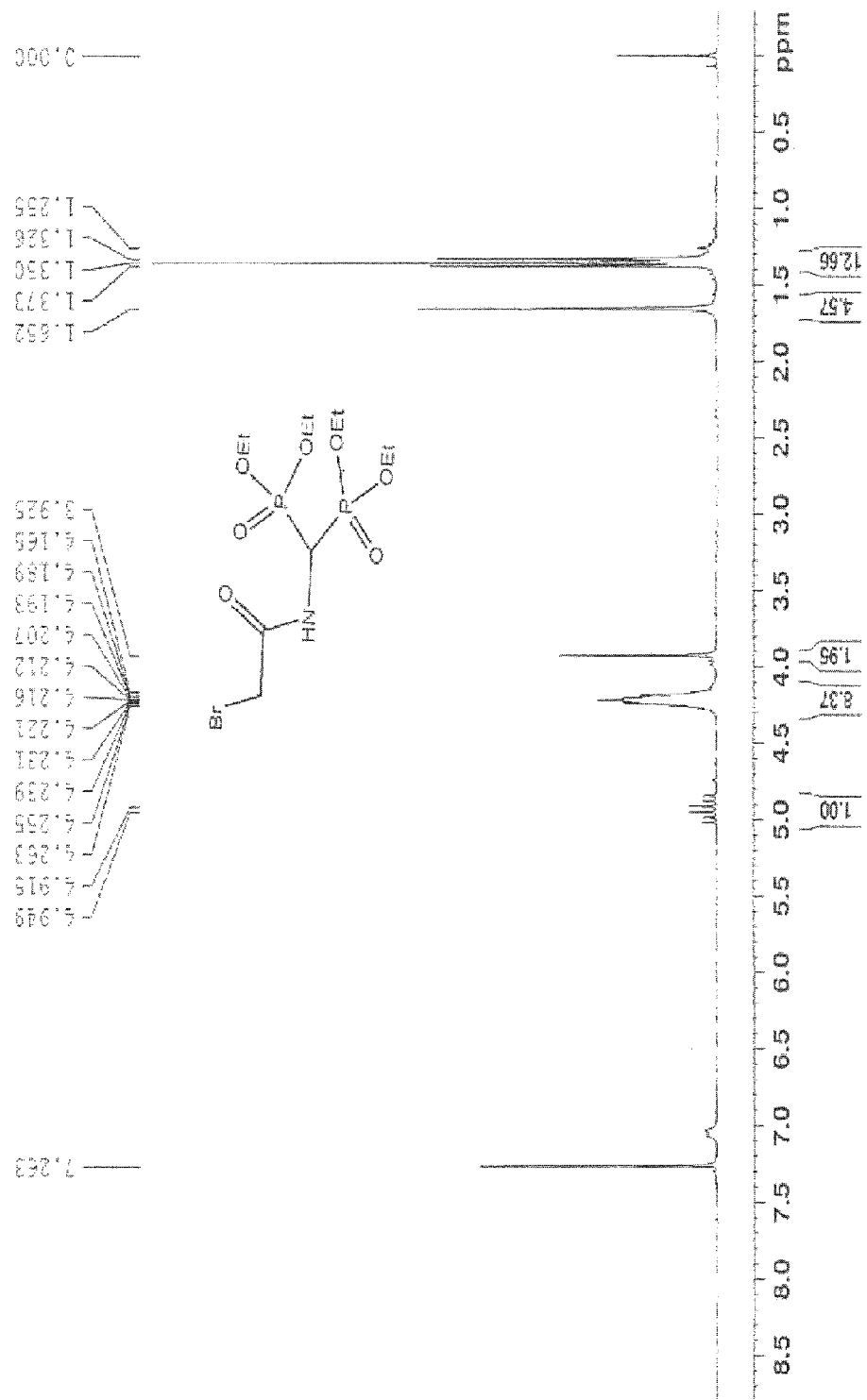
FIG. 2 shows $^1$H-spectra of bromoacetyl-AMDP-ester.

4.1 g (38.6 mmol) of sodium carbonate was added in a solution of AMDP ester (2 g, 6.6 mmol) in acetonitrile, and the mixture was cooled at −40° C. 4.26 g (21.1 mmol) of Bromoacetyl bromide was added dropwise to this cooled solution. Then the mixture was heated to room temperature and stirred for overnight (15 hours). Next, the solid part and the solvent part were separated, and the solvent part was then evaporated under reduced pressure condition to give a crude product. The crude product was underwent repeated evaporation with toluene. The product was 2.65 g Bromo-acetyl-AMDP-ester. FIG. 2 showed proton NMR spectrum of bromoacetyl-AMDP-ester (δ 7.2, singlet; δ 4.9, doublet; δ 4.1-4.3, broad multiplet; δ 3.9, singlet; δ 1.6, singlet; δ 1.2-1.4, quartet).

Example 2. Synthesis of N6-carboxymethyl-N3,N9-bis[[[4,4-bis (phosphono)methyl]carbamoyl]methyl]-3,6,9-triazaundecanedioic acid (DTPA-AMDP)

The two-step synthesis of DTPA-AMDP is shown in Scheme 2.

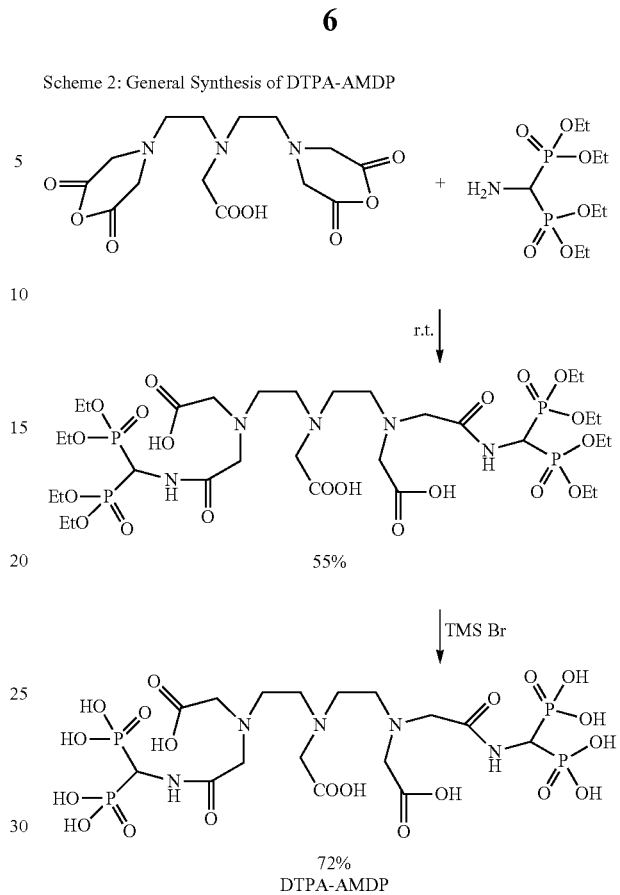

Scheme 2: General Synthesis of DTPA-AMDP

Figure 3:
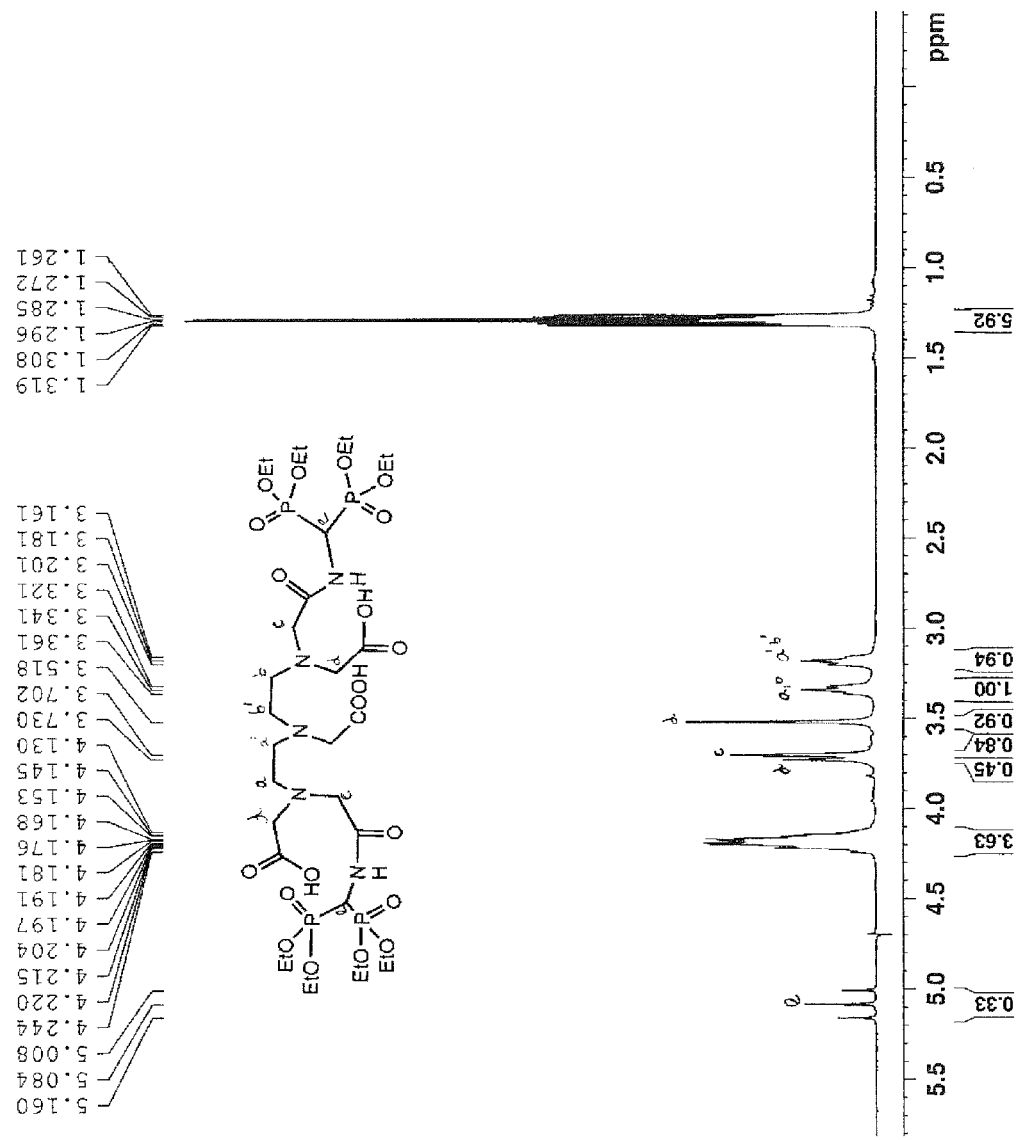
FIG. 3 shows $^1$H NMR-spectra of DTPA-AMDP (ester).
Figure 4:
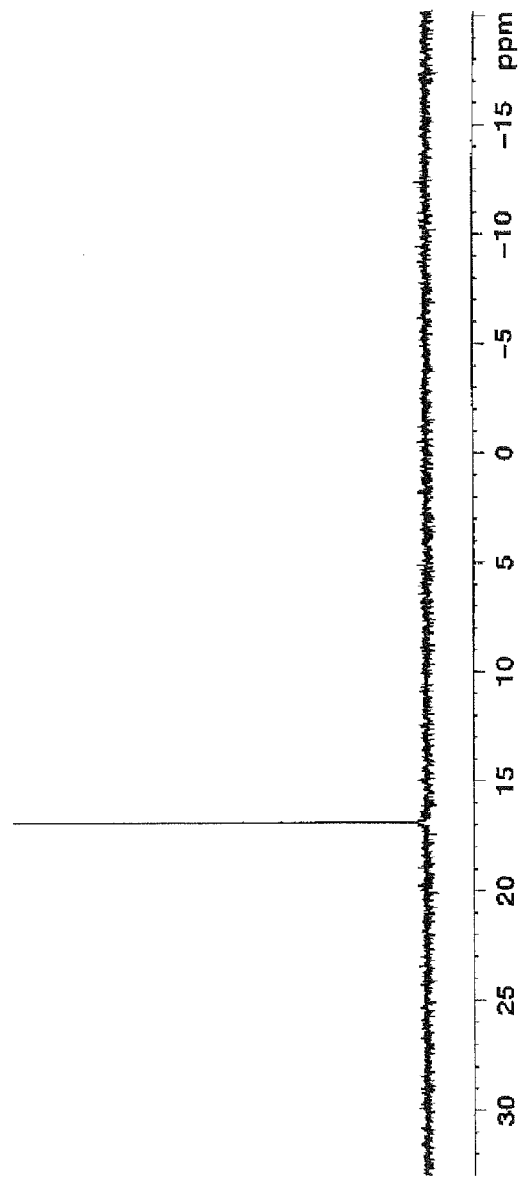
FIG. 4 shows $^{31}$P NMR-spectra of DTPA-AMDP (ester).
Figure 5:
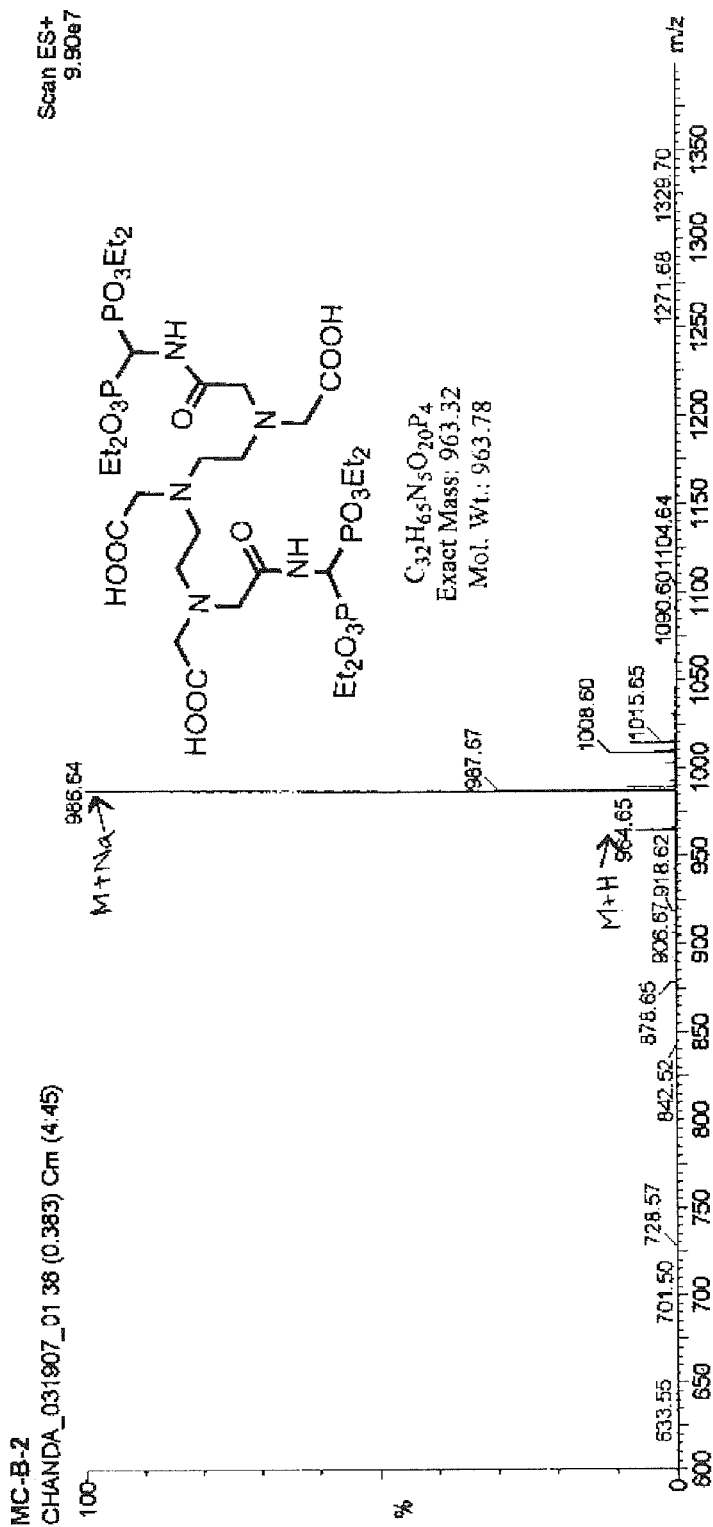
FIG. 5 shows Mass spectra of DTPA-AMDP (ester).

Step a. Conjugation-synthesis of N6-carboxymethyl-N3,N9-bis [[[4,4-bis(phosphonoethyl)methyl]carbamoyl]methyl]-3,6,9-triazaundecane dioic acid (DTPA-AMDP-ester) conjugate AMDP ester 0.545 g (1.798 mmol) was dissolved in 20 ml of anhydrous DMF. 20 ml suspension of diethylenetriaminepentaacetic dianhydride (DTPA) in DMF was added to the AMDP ester solution under nitrogen atmosphere, and the mixture was stirred at room temperature for 16 hours. 5 ml of water was added and the mixture was stirred for another 4.5 hour at room temperature. Solvent was evaporated under reduced pressure condition and the residue was purified by using gel filtration Sephadex G15 as medium to obtain 480 mg DTPA-AMDP ester product. The structure of DTPA-AMDP ester was confirmed by proton NMR (FIG. 3, δ 5-5.2, triplet; δ 4.1-4.5 broad multiplet; δ 3.73, singlet; δ 3.70, singlet; δ 3.5, singlet; δ 3.2-3.6, broad triplet; δ 3.1-3.5, broad triplet), $^{31}$P NMR (FIG. 4, δ 16.8) and mass spectrometry (FIG. 5).

Step b. De-Esterification of DTPA-AMDP-Ester Conjugate

Figure 6:
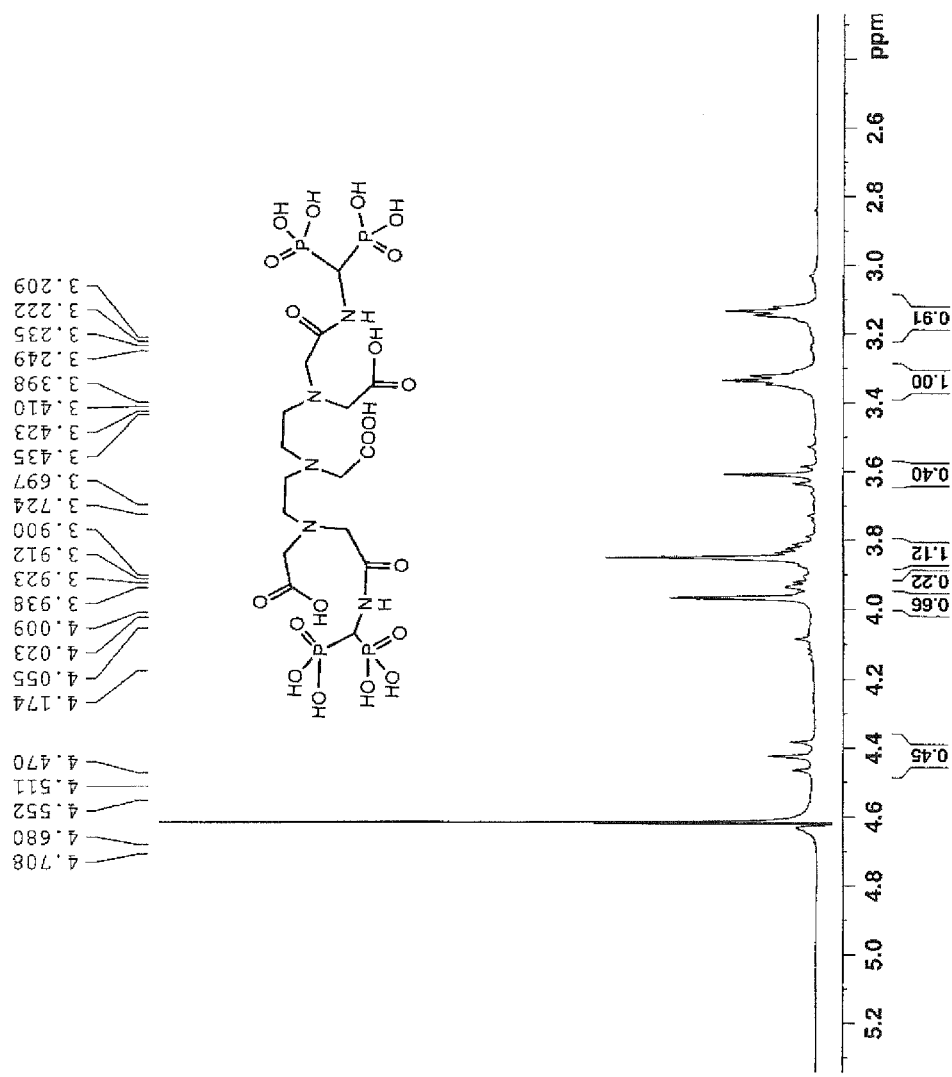
FIG. 6 shows $^1$H NMR-spectra of DTPA-AMDP.
Figure 7:
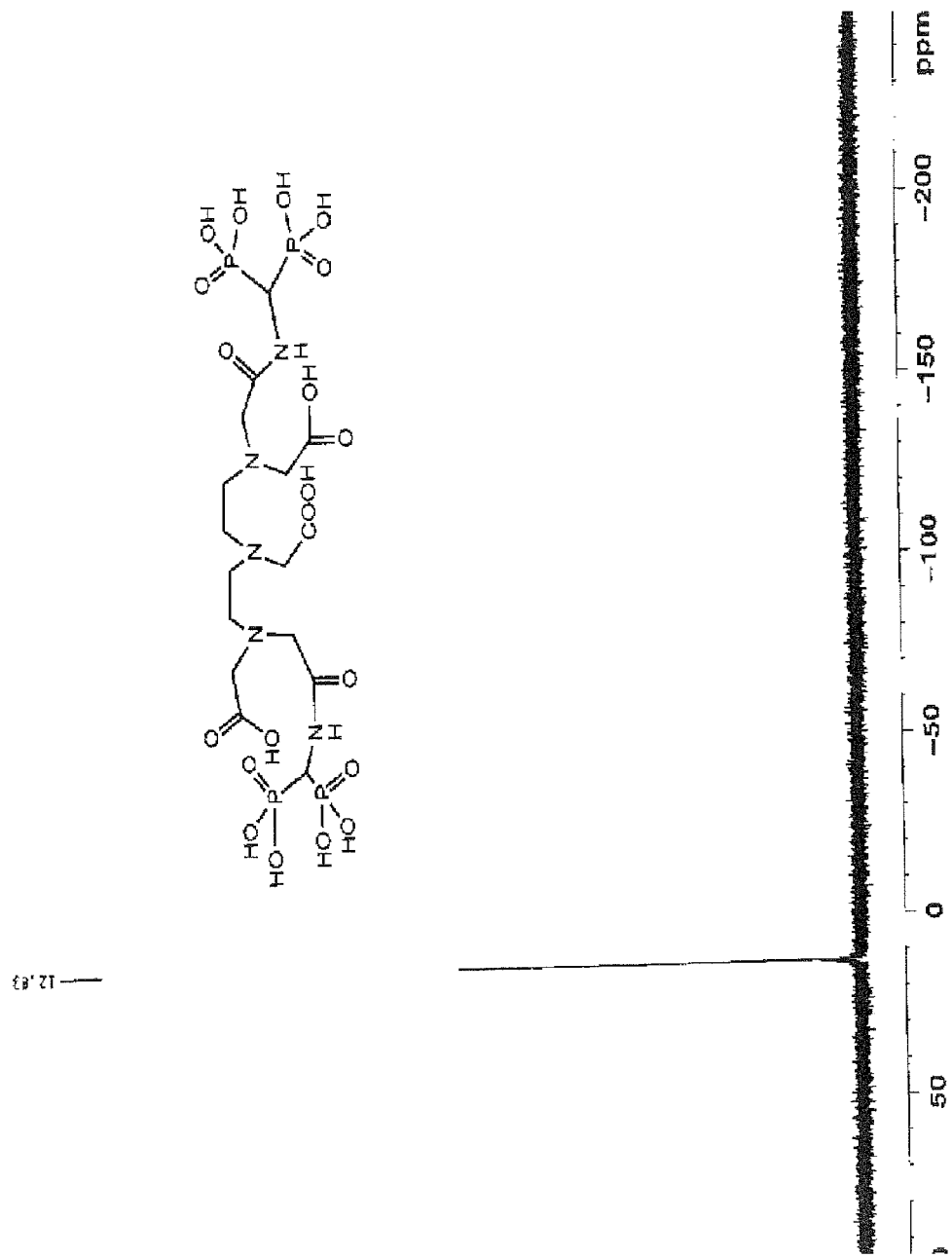
FIG. 7 shows $^{31}$P NMR-spectra of DTPA-AMDP.
Figure 8:
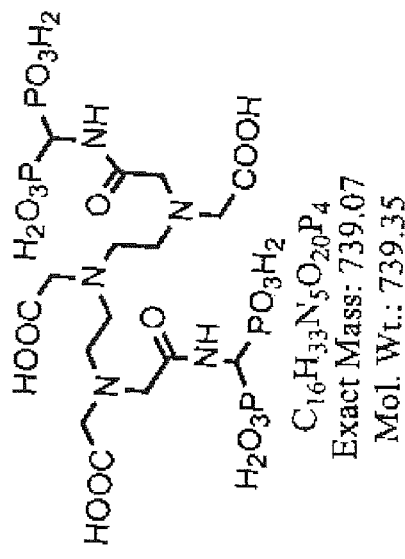
FIG. 8 shows Mass spectra of DTPA-AMDP.
Figure 8:
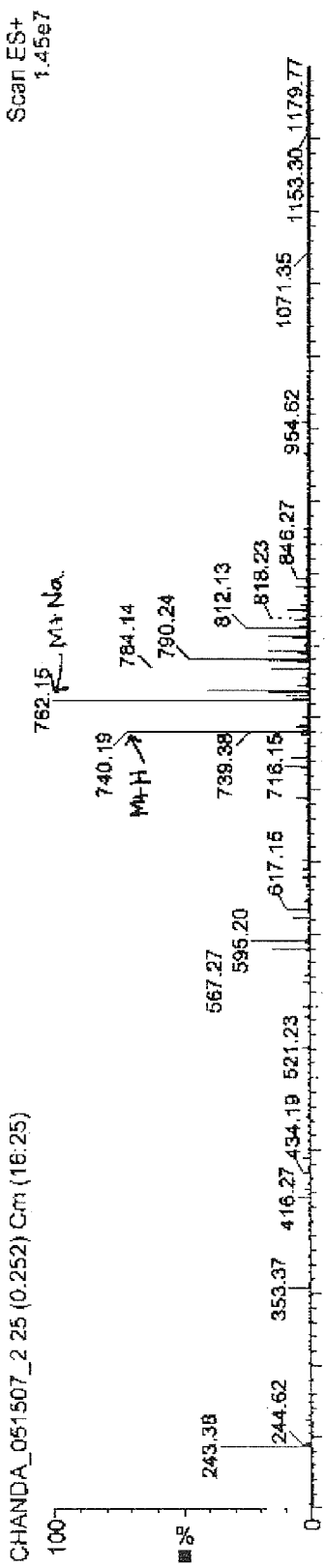

A solution of 0.26 g (0.2697 mmol) DTPA-AMDP ester was cooled in methylene chloride at 0° C., and was slowly added 1.14 ml (8.63 mmol) bromotrimethyl silane under nitrogen atmosphere. The mixture was stirred at room temperature for 29 hours. Volatiles were evaporated under reduced pressure condition. The residue was cooled, hydrolyzed with 6 ml of water, and stirred for 15 min. The resulting solution was lyophilized and purified by sephadex, then obtained the final product 140 mg DTPA-AMDP. The structure of the final product was confirmed by proton NMR (FIG. 6), $^{31}$P NMR (FIG. 7, δ 12.8), and Mass spectrometry (FIG. 8)

Example 3. Synthesis of N6-carboxymethyl-N3,N9-bis[[2,2-bis (phosphono)-2-hydroxy]ethyl]-3,6,9-triazaundecanedioic acid (DTPA-BP)

The synthesis of DTPA-BP is shown in Scheme 3.

Scheme 3: General Synthesis of DTPA-BP

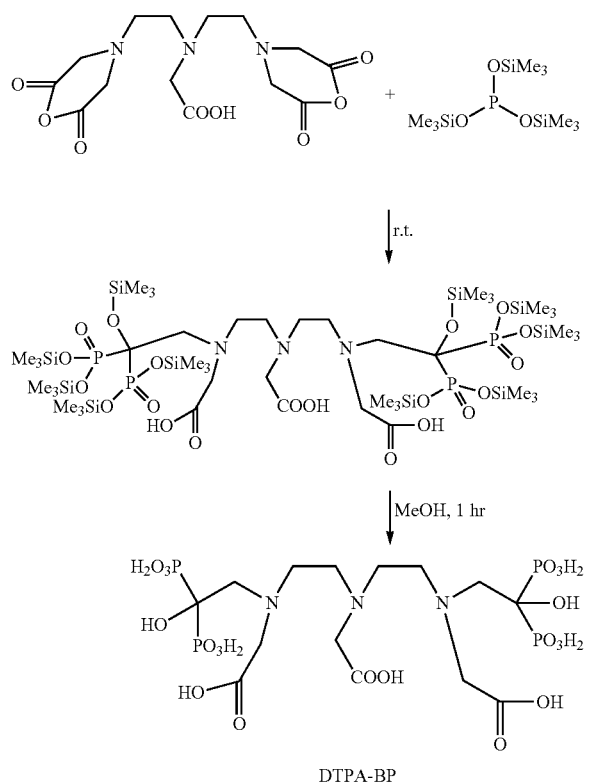

DTPA-BP

Figure 9:
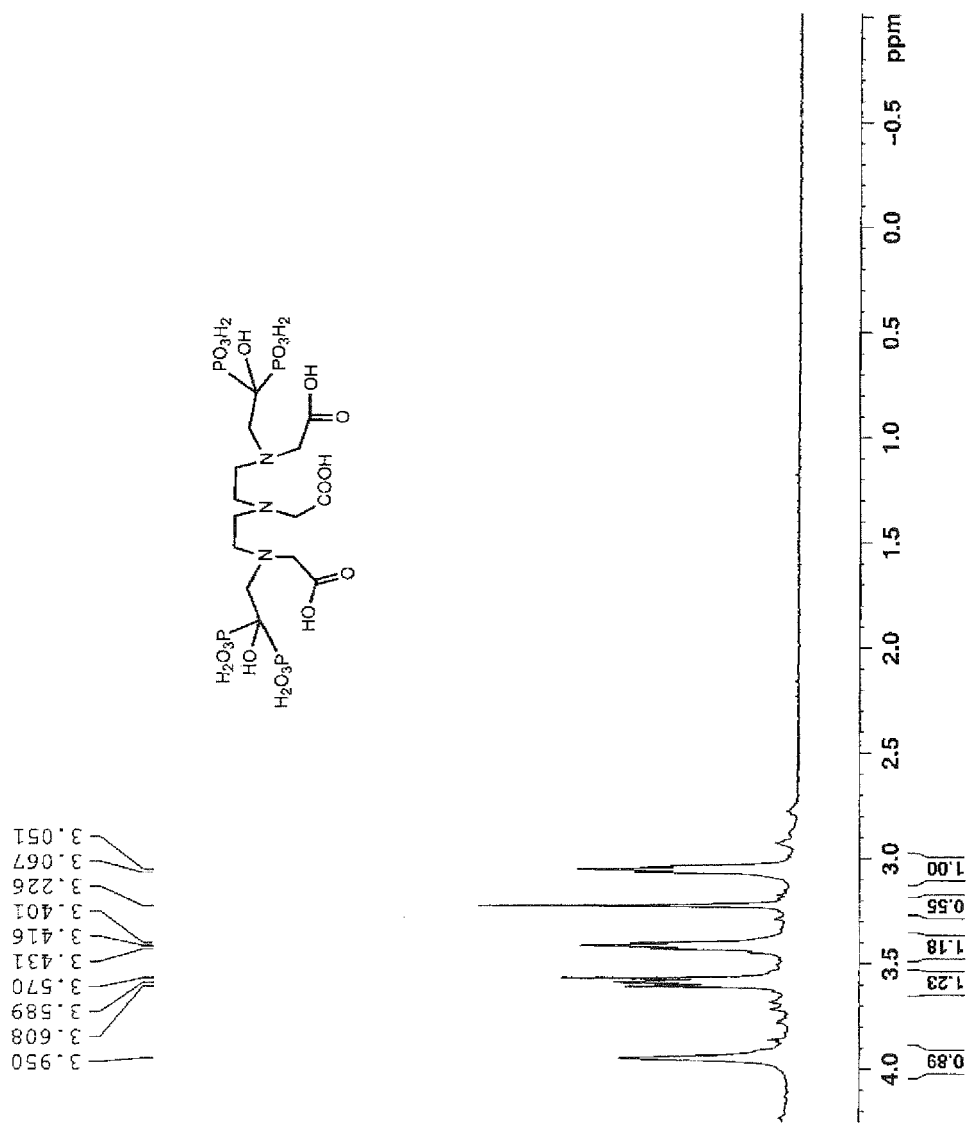
FIG. 9 shows $^1$H NMR-spectra of DTPA-BP.
Figure 10:
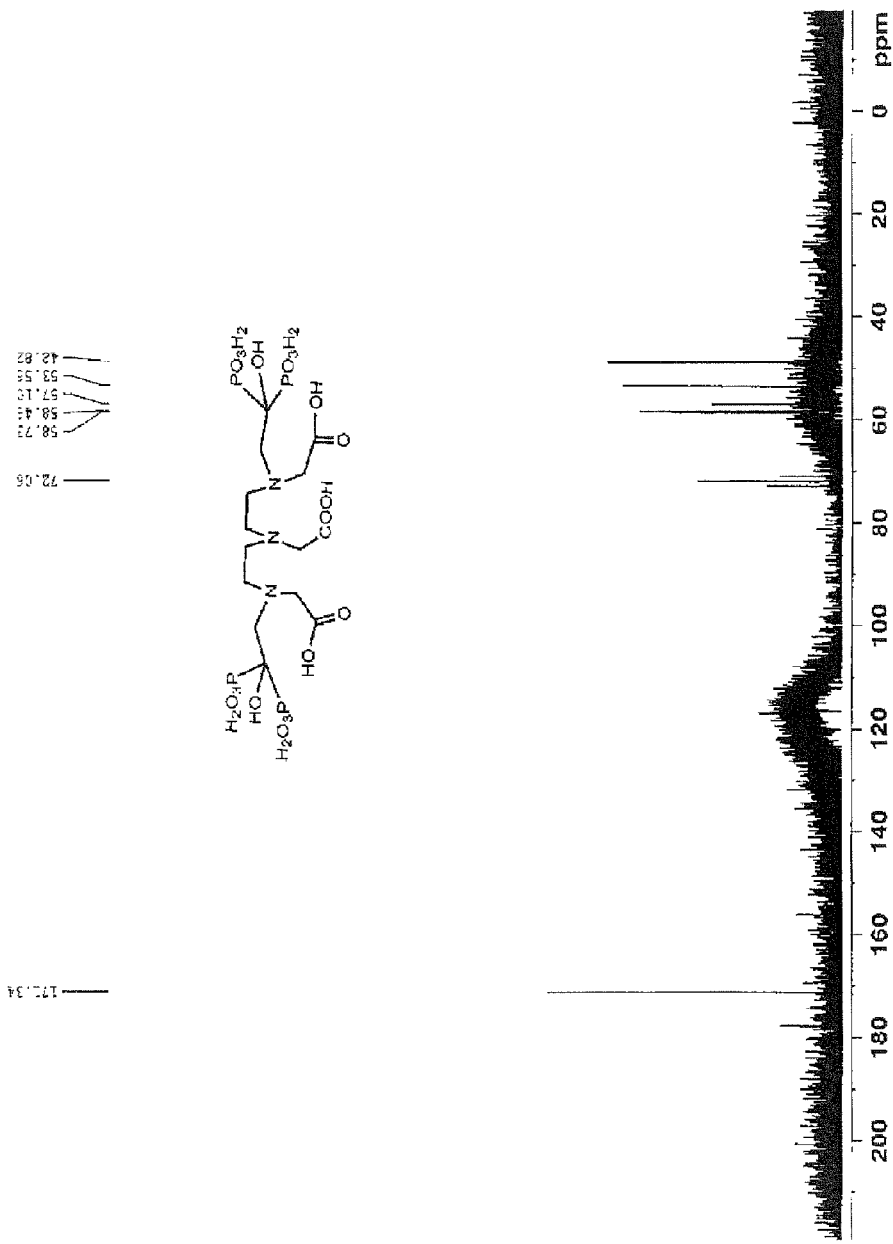
FIG. 10 shows $^{13}$C NMR-spectra of DTPA-BP.
Figure 11:
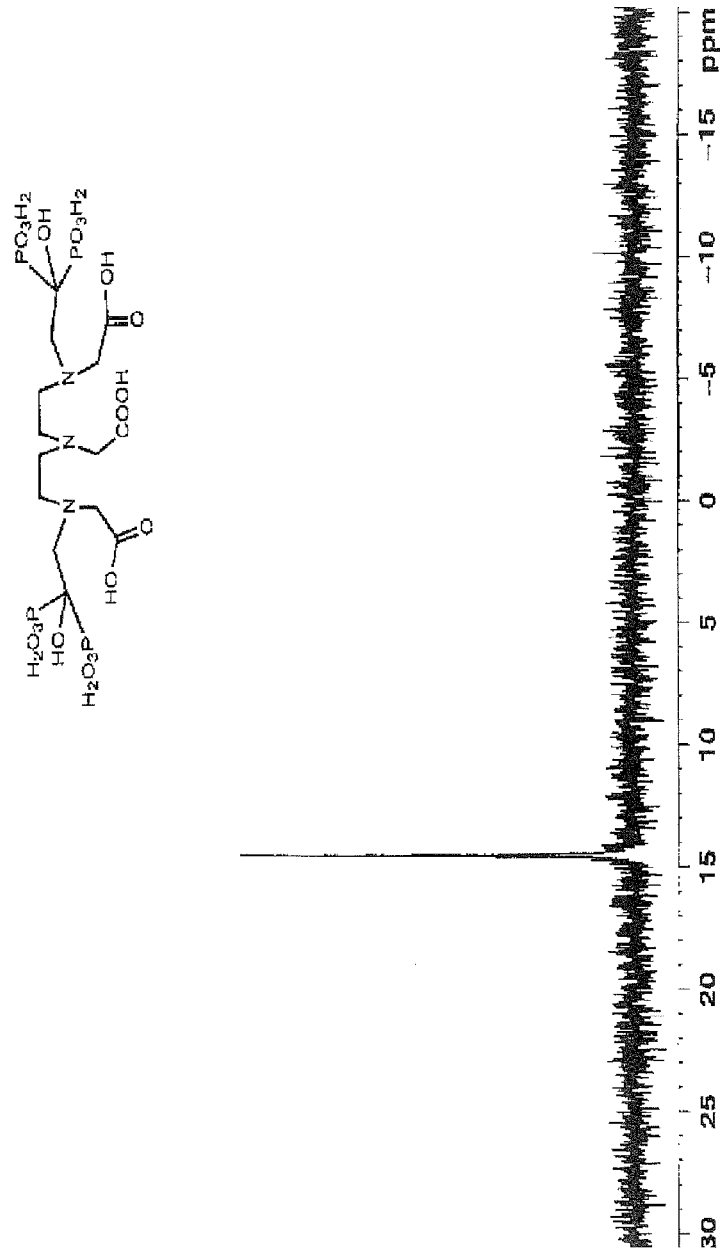
FIG. 11 shows $^{31}$P NMR-spectra of DTPA-BP.
Figure 12:
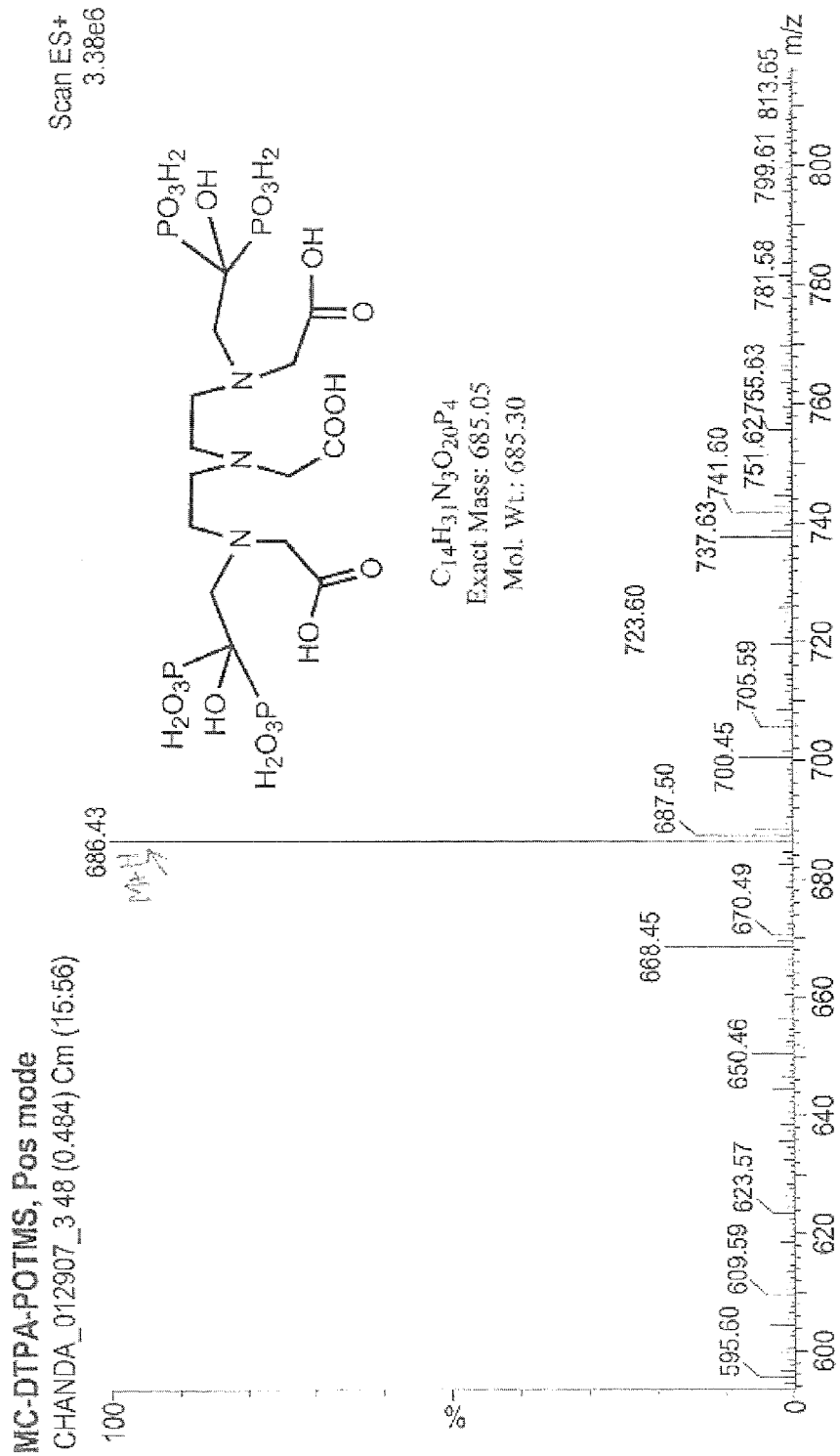
FIG. 12 shows Mass spectra of DTPA-BP.

In this reaction, 0.48 g (1.34 mmol) of DTPA in 1 ml of THF was added to 1.8 ml (5.38 mmol) of tris(trimethylsilyl) phosphite under N$_2$ atmosphere, and the mixture was stirred for 14 hours at room temperature. Volatiles were evaporated under reduced pressure condition. The thick residue was cooled, hydrolyzed with 10 ml of methanol, and stirred at room temperature for 1 hour. The mixture was filtered to separate the solid part and the solvent part. Then the white solid part was washed by methanol and ether and purified by sephadex to obtain 83 mg product DTPA-BP. The structure of the product was confirmed by proton NMR (FIG. 9, δ 3.9, singlet; δ 3.5, triplet; δ 3.4, broad triplet; δ 3.2, singlet; δ 3.0, doublet), $^{13}$C NMR (FIG. 10, δ 171; δ 72; δ 58; δ 53; δ 42), $^{31}$P NMR (FIG. 11, δ 14.5) and mass spectrometry (FIG. 12).

Example 4. Synthesis of N-[2-(Tritylthio)ethyl]-2-[2-(tritylthio) ethylamino]acetamide (MAMA-DS (Tr))

The synthesis of MAMA-DS(Tr) is shown in Scheme 4.

Scheme 4: General Synthesis of MAMA-DS(Tr)

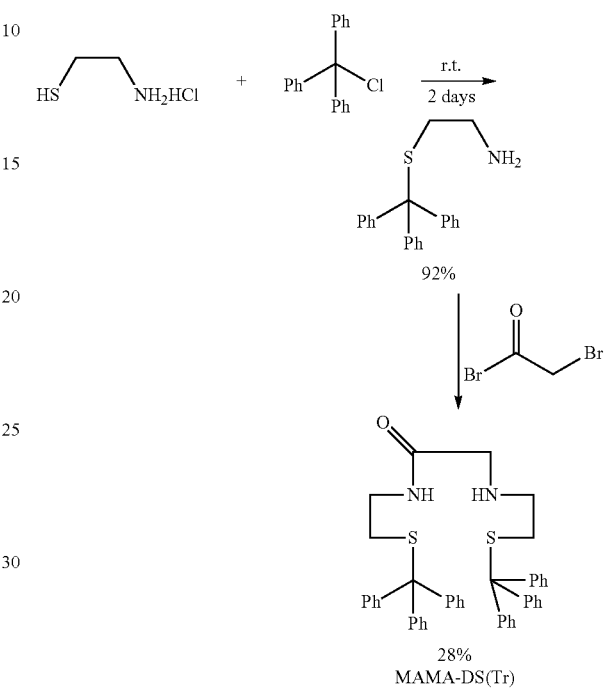

MAMA-DS(Tr)

Figure 13:
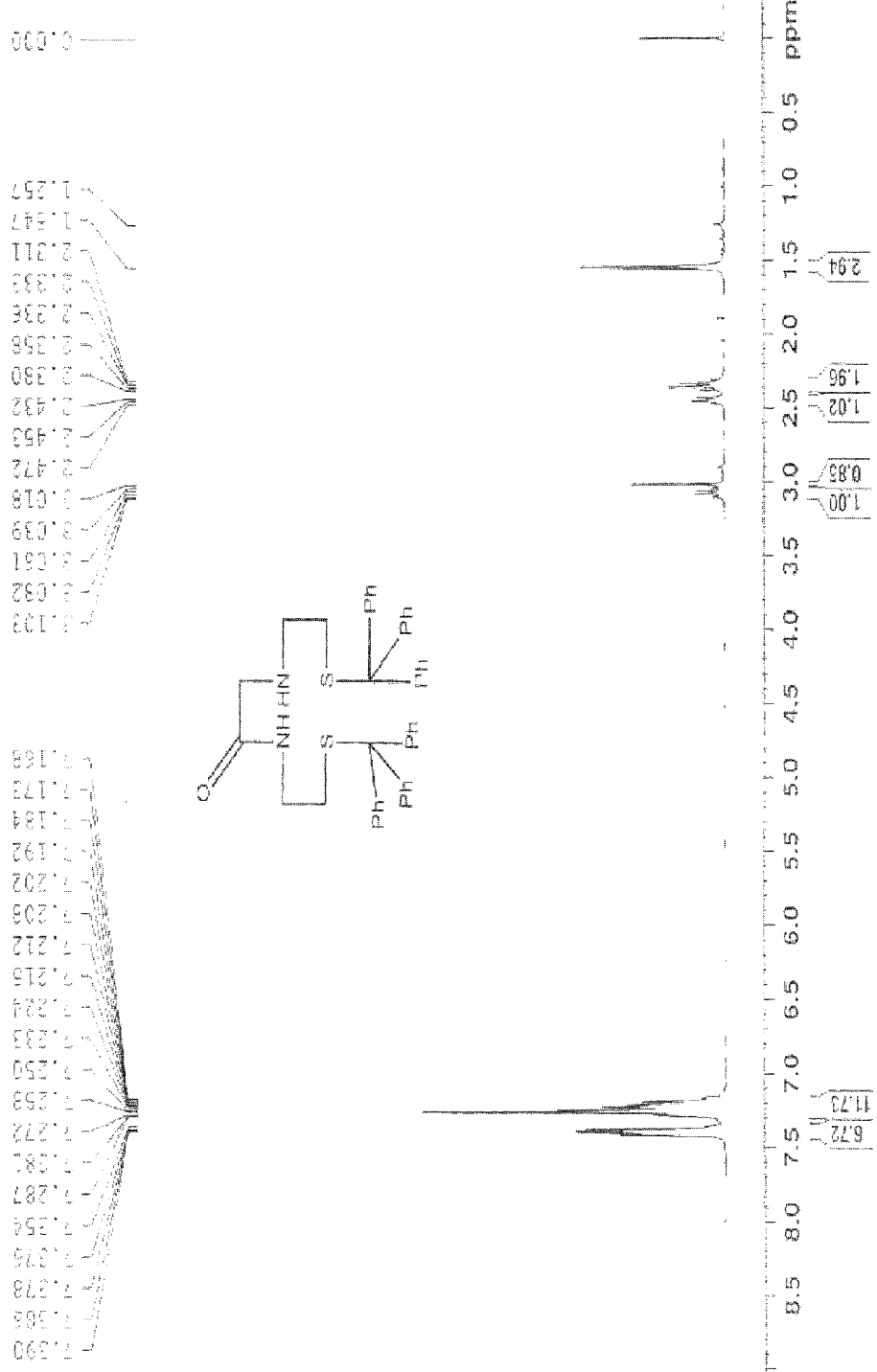
FIG. 13 shows $^1$H NMR-spectra of MAMA-DS (Tr).

In this reaction, 4.44 g of aminoethanethiol hydrochloride 4.44 g (39 mmol) was dissolved in 60 ml of DMF. 10.92 g of trityl chloride was added into the solution, and the mixture was stirred at room temperature for 48 hours. The solvent was evaporated under reduced pressure condition, and the residue was washed by ethyl acetate. The resulting solution was filtered to separate the solid part and the solvent part. Then the solid part was suspended in water and pH was adjusted to 8. Finally, drying the solid to obtain the crude product 13.5 g. Crude product 6 g (16.90 mmol) was then dissolved in chloroform and added to 8.23 ml of triethyl amine. This solution was added dropwise to the bromoacetyl bromide 0.632 g (3.13 mmol) solution in chloroform at −78° C., and the mixture was stirred at the same temperature for 30 minutes. Next, the mixture was heated to room temperature and stirred overnight. The resulting solution was washed with water. Once the water layer and organic layer were separated, the organic layer was isolated, dried and solvent was removed to get the crude. Then the crude was purified by silica gel column chromatography. The product was 3.2 g MAMA-DS (Tr). FIG. 13 showed the proton NMR spectra of MAMA-DS (Tr) (δ7.3, broad quartet; δ7.2, broad multiplet, δ3.06, quartet; δ 3.01, singlet; δ 2.4, triplet; δ 2.3, quintet; δ 1.5, singlet).

Example 5. Synthesis of N-[2-[[3-(3,3-Diphosphonomethylcarbamoyl) ethyl](2thioethyl)amino]acetyl]-2-aminoethanethiol (MAMA-DS-AMDP)

MAMA-DS-AMDP was synthesized in 2 steps as shown in Scheme 5.

Scheme 5: General Synthesis of MAMA-DS-AMDP

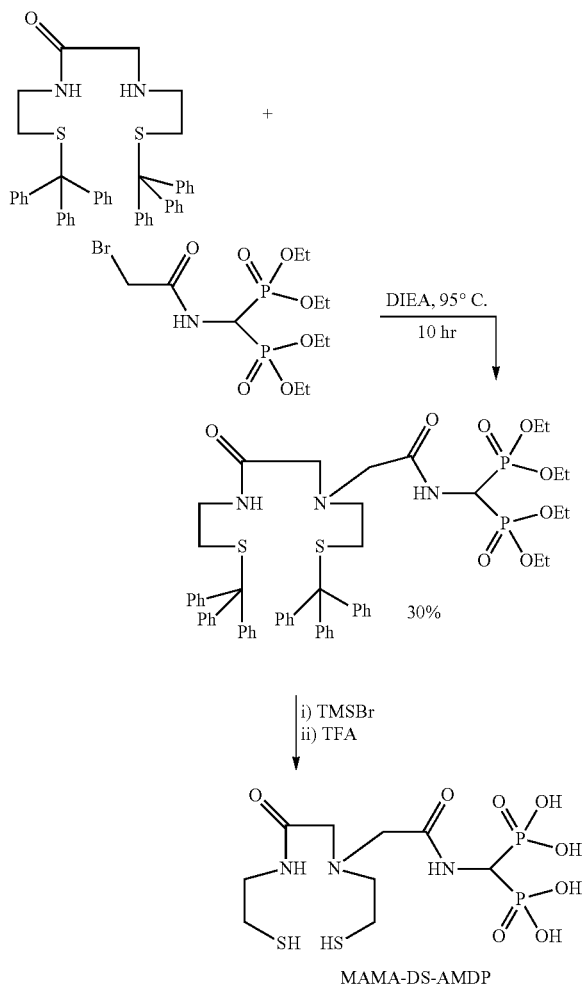

MAMA-DS-AMDP

Step a. Conjugation of Bromoacetyl-AMDP-Ester with MAMA-DS (Tr)

Figure 14:
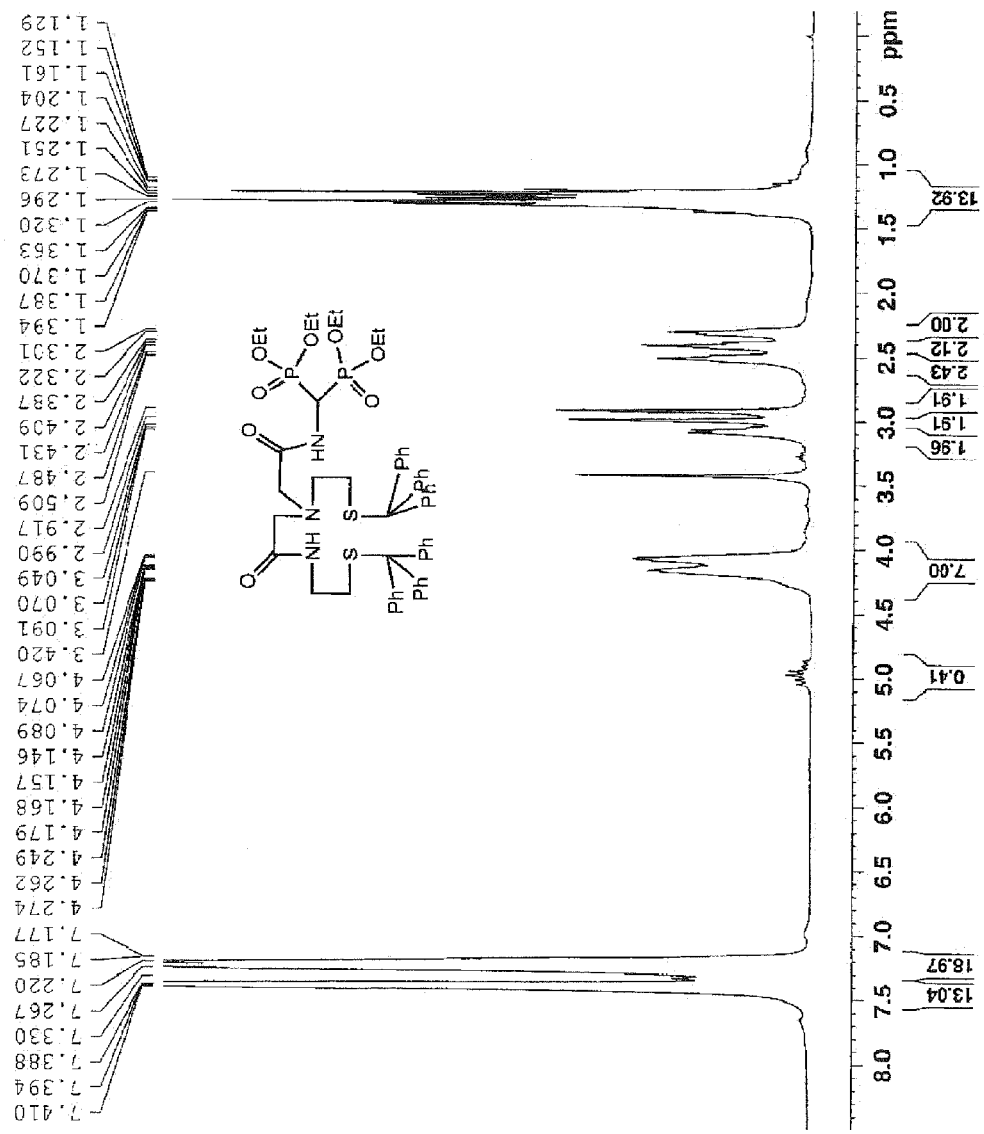
FIG. 14 shows $^1$H NMR-spectra of MAMA-DS (Tr)-AMDP ester.
Figure 15:
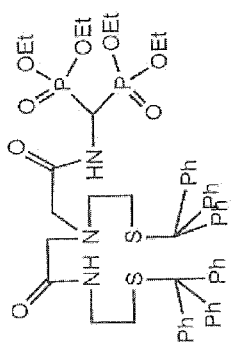
FIG. 15 shows $^{31}$P NMR-spectra of MAMA-DS (Tr)-AMDP ester.
Figure 15:
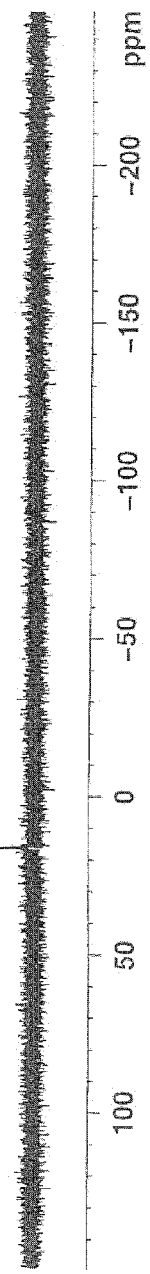
Figure 16:
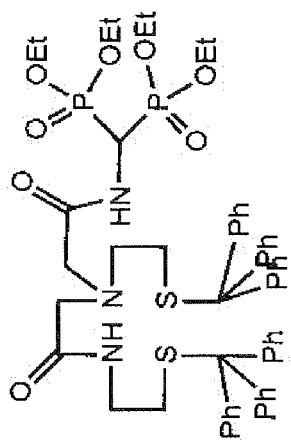
FIG. 16 shows Mass spectra of MAMA-DS (Tr)-AMDP ester.
Figure 16:
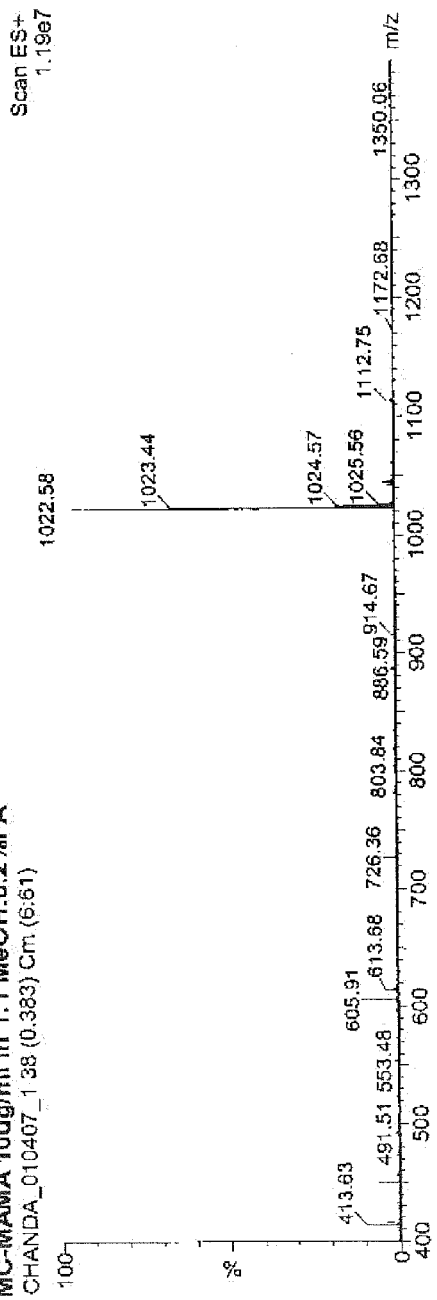

0.6 g (0.88 mmol) of MAMA-DS (Tr) (product of Example 4) was dissolved in DMF. 0.45 g (1.05 mmol) of bromoacetyl-AMDP-ester obtained in Example 1 followed by 0.184 ml of Diisopropylethylamine was added. The resulting mixture was heated at 95° C. for 15 hours. Then the solvent was evaporated under reduced pressure condition, and the residue was purified by silica gel column. The product is 267 mg MAMA-DS (Tr)-AMDP ester. The structure was confirmed by proton NMR (FIG. 14, δ 7.3, triplet; δ 7.1, quartet; δ 5; δ 4.1; broad multiplet), $^{31}$P NMR (FIG. 15) and mass spectrometry (FIG. 16).

Figure 17:
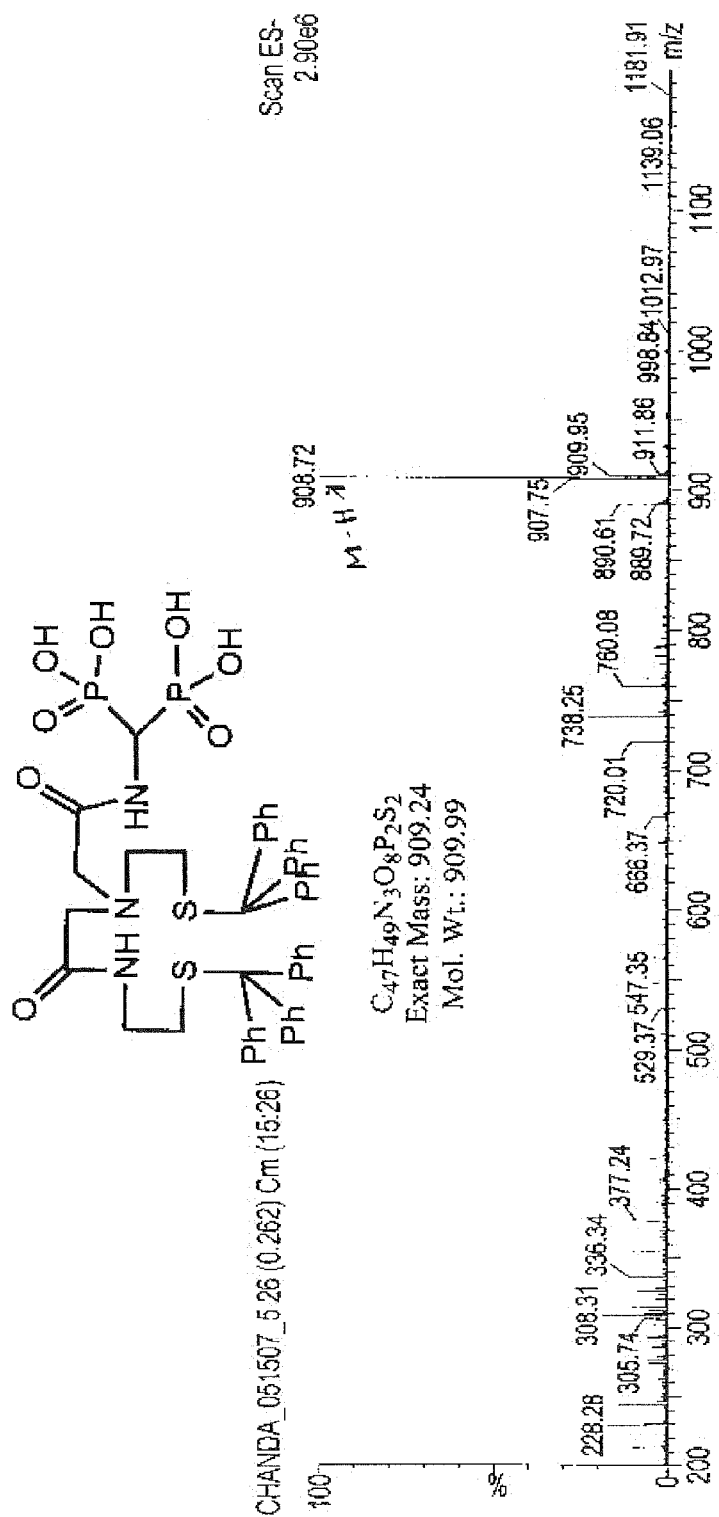
FIG. 17 shows Mass spectra of MAMA-DS (Tr)-AMDP.
Figure 18:
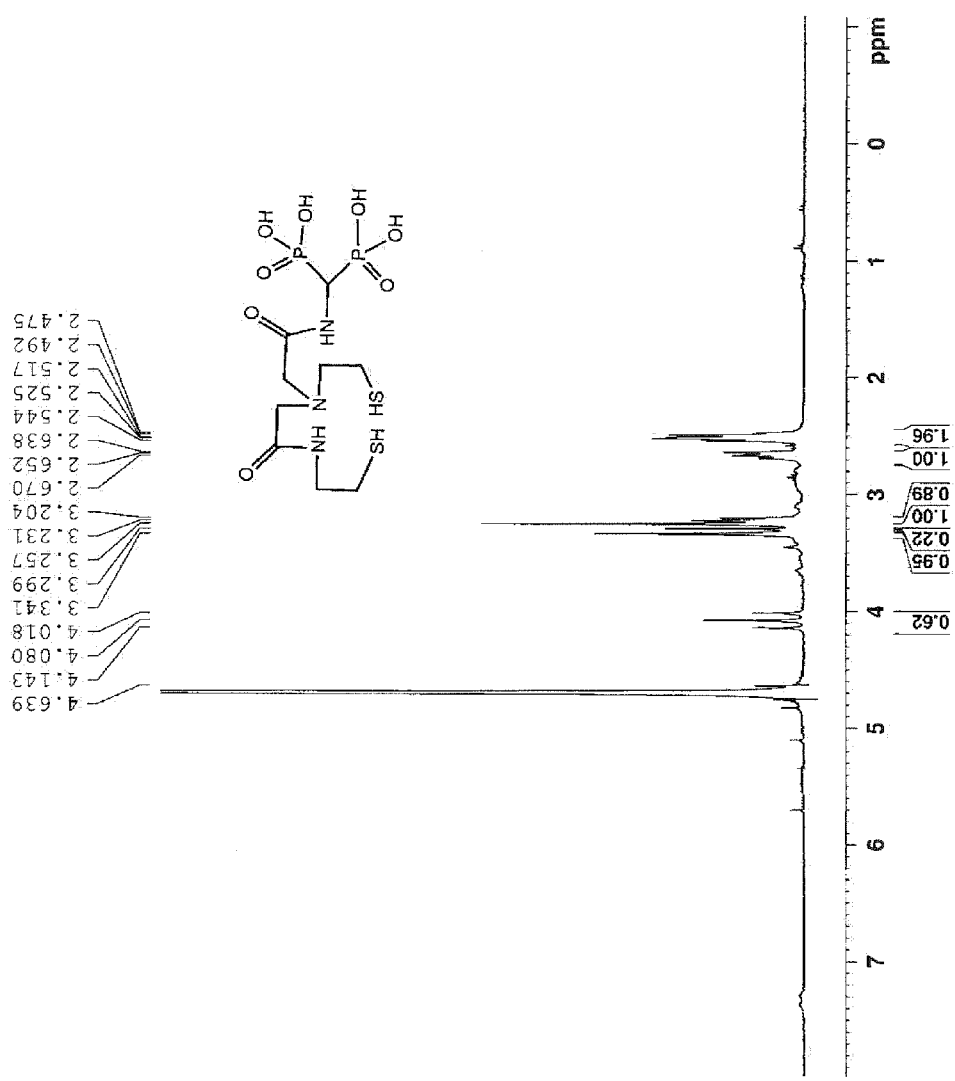
FIG. 18 shows $^1$H NMR-spectra of MAMA-DS-AMDP.
Figure 19:
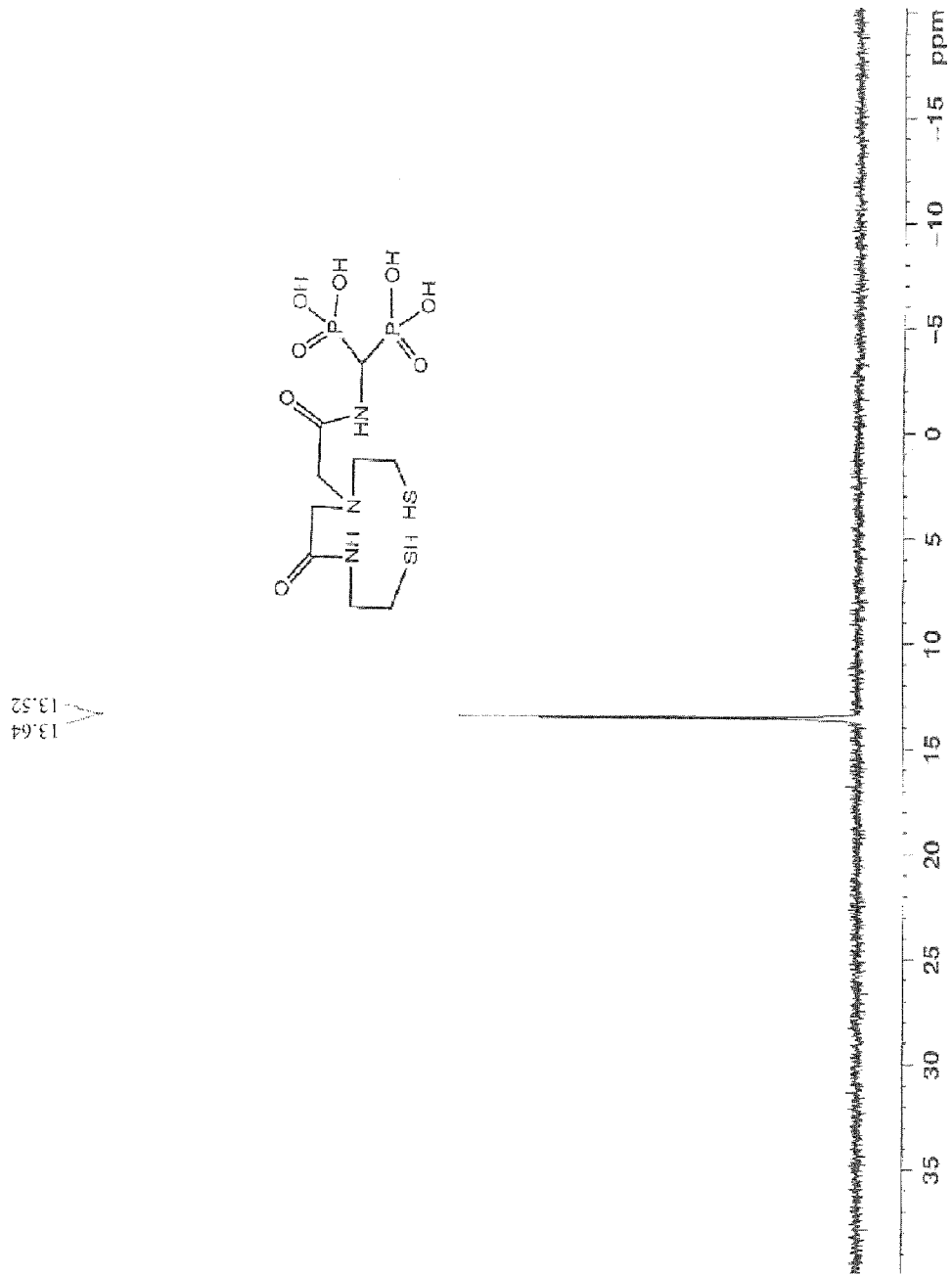
FIG. 19 shows $^{31}$P NMR-spectra of MAMA-DS-AMDP.

Step b. Deprotection of Trityl and Ethyl Ester Group 150 mg (0.146 mmol) of MAMA-DS (Tr)-AMDP ester was dissolved in chloroform. 0.15 ml (1.16 mmol) of Trimethylsilyl bromide was added into the solution and the mixture was stirred at 45° C. for 2.5 hours following by stirring at room temperature for 40 hours. Then solvent was evaporated and 2.5 ml of methanol was added to the crude. The resulted solution was then stirred for 2.5 hours. After that, methanol was removed, the precipitate was dried to obtain 90 mg (yield 67%) of MAMA-DS (Tr)-AMDP. FIG. 17 shows the mass peaks of the deesterified product. Next, 10 mg (0.01 mmol) of deesterified product was dissolved in 200 μL of TFA and stirred for 5 minutes. Then, triethylsilane was added. After evaporating volatiles, the crude product could be used for radio labeling. FIG. 18 (δ 4.0, triplet; δ 3.2, quintet; δ 2.6, doublet; δ 2.5, quartet) and FIG. 19 (δ 13) showed the $^1$H and $^{31}$P NMR spectra of MAMA-DS-AMDP.

Example 6. Synthesis of 1,4,8,11-Tetraazacyclotetradecane-1,4,8,11-tetrakis(3-hydroxy-propylenebisphosphonate) (OB-142)

OB-142 was synthesized in a 3-step manner. The synthesis is shown in Scheme 6.

Scheme 6: General Synthesis of OB142

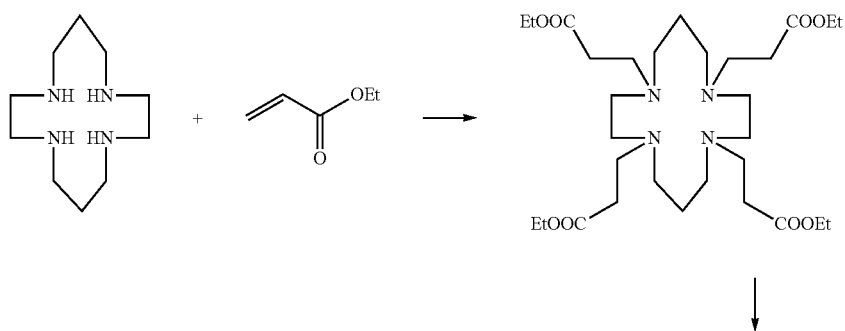

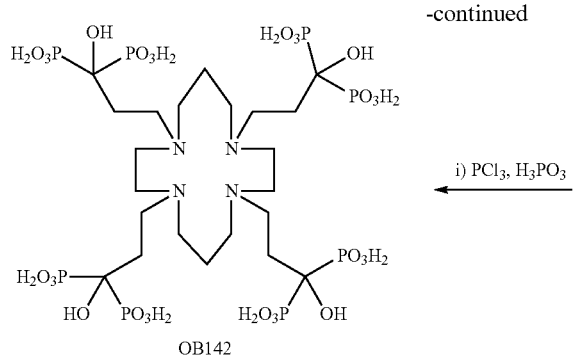 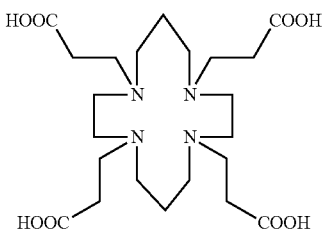

Some exemplary structures of tetraazacyclic bisphosphonates are shown below:

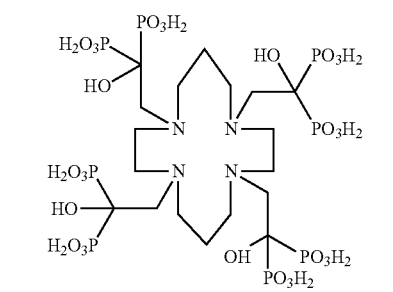

OB-141

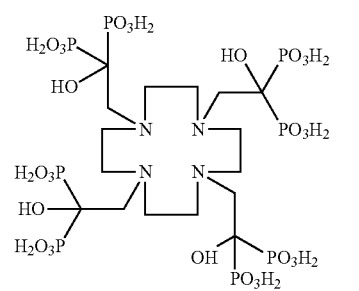

OB-121

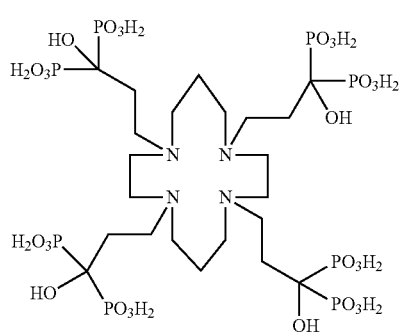

OB-142

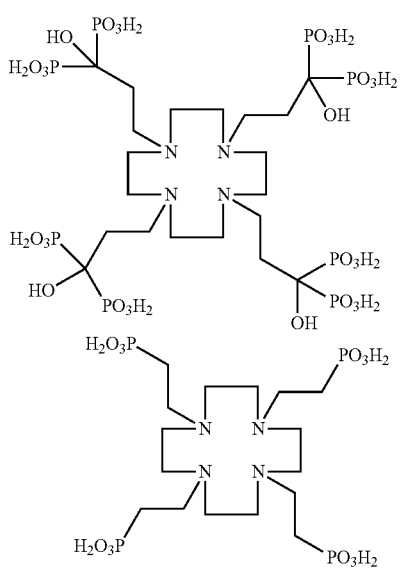

OB-122

OMS(Control)

Step a. Synthesis of 1,4,8,11-Tetraazacyclotetradecane-1,4,8,11-tetrapropanoic acid ethyl ester In this reaction, 2.003 mg (10 mmol) of 1,4,8,11-Tetraazacyclotetradecane, 324.4 mg of $FeCl_3$ (2 mmol) in 50 mL of acetonitrile and 4348 μL of Ethyl acrylate (40 mmol) were mixed and stirred at room temperature for 48 hours. Then low boiling material was evaporated under reduced pressure condition. The residue was isolated by silica-gel column chromatography using gradient solvent system (chloroform:methanol=100:1-10:5) to obtain 4.085 g of pale yellow 1,4,8,11-Tetraazacyclotetradecane-1,4,8,11-tetrapropanoic acid ethyl ester.

Step b. Synthesis of 1,4,8,11-Tetraazacyclotetradecane-1,4,8,11-tetrapropanoic acid The solution of 3.604 g of 1,4,8,11-Tetraazacyclotetradecane-1,4,8,11-tetrapropanoic acid ethyl ester (6 mmol) in 3 mL of ethyl alcohol was added to 20 mL of 4-N sodium hydroxide (80 mmol). The reaction mixture was heated at 60° C. for 1 hour and then low boiling material was evaporated. The residue was isolated with Sephadex-G75 to get 2.594 g of 1,4,8,11-Tetraazacyclotetradecane-1,4,8,11-tetrapropanoic acid tetra sodium salt.

Step c. Synthesis of 1,4,8,11-Tetraazacyclotetradecane-1,4,8,11-tetrakis (3-hydroxy-propylenebisphosphonate)

2.306 g of 1,4,8,11-Tetraazacyclotetradecane-1,4,8,11-tetrapropanoic acid (4 mmol) was dissolved in the solution of 1368 µL of 85% phosphorous acid (24 mmol as a 85% phosphorous acid) and 6.7 mL of chlorobenzene in 20 mL 2-neck flask equipped with caustic gas scrubber, reflux condenser, and additional funnel. Then the mixture was pre-heated around 100-110° C. 1745 µL (20 mmol) of trichlorophosphine was added to the hot mixture drop by drop for 15 min to 1 hour.

Then a thick precipitate was formed. After heating the mixture for overnight followed by cooling down it, the bulk of the chlorobenzene was decanted, and the remaining solvent was evaporated under reduced pressure condition. The white or yellow residue was taken up in 10 mL of water and heated to reflux for 1 hour.

1.3159 g of sodium hydroxide was added to the mixture at room temperature. The pH was adjusted around 5 and an orange turbid material was obtained. Then, further 1.6952 g of sodium hydroxide was added into the mixture. The orange turbid material turned to brown when pH became 10. The mixture was filtered with 0.45 µm nylon membrane, and then the filtrate was dialyzed with a membrane, wherein the molecular weight cut off (MWCO) of the membrane was less than 500 Daltons. The product was lyophilized and isolated with Sephadex G-75 to get 2.059 g of 1,4,8,11-Tetraazacyclotetradecane-1,4,8,11-tetrakis(2-hydroxy-propylenebisphosphonate).

Example 7. Synthesis of 1,4,7,10-Tetraazacyclododecane-1,4,7,10-tetrakis(2-hydroxy-ethylenebisphosphonate) (OB-121)

510.7 mg (1.0 mmol) of DOTA (1,4,7,10-Tetraazacyclododecane-1,4,7,10-tetraacetic acid; MW 510.7, including 5.9 mol $H_2O$) was dissolved in the solution of 1368 µL of 85% phosphorous acid (24 mmol as a 85% phosphorous acid) and 6.7 mL of chlorobenzene in 20 mL 2-neck flask equipped with caustic gas scrubber, reflux condenser, and additional funnel. Then the mixture was pre-heated around 100-110° C. 1745 µL (20 mmol) of trichlorophosphine was added dropwise to the hot mixture.

Then a thick precipitate was formed. After heating the mixture overnight and then cooled down it, the bulk of the chlorobenzene was decanted, and the remaining solvent was evaporated under reduced pressure condition. The white or yellow residue was taken up in 10 mL of water and heated to reflux for 1 hour.

Figure 20:
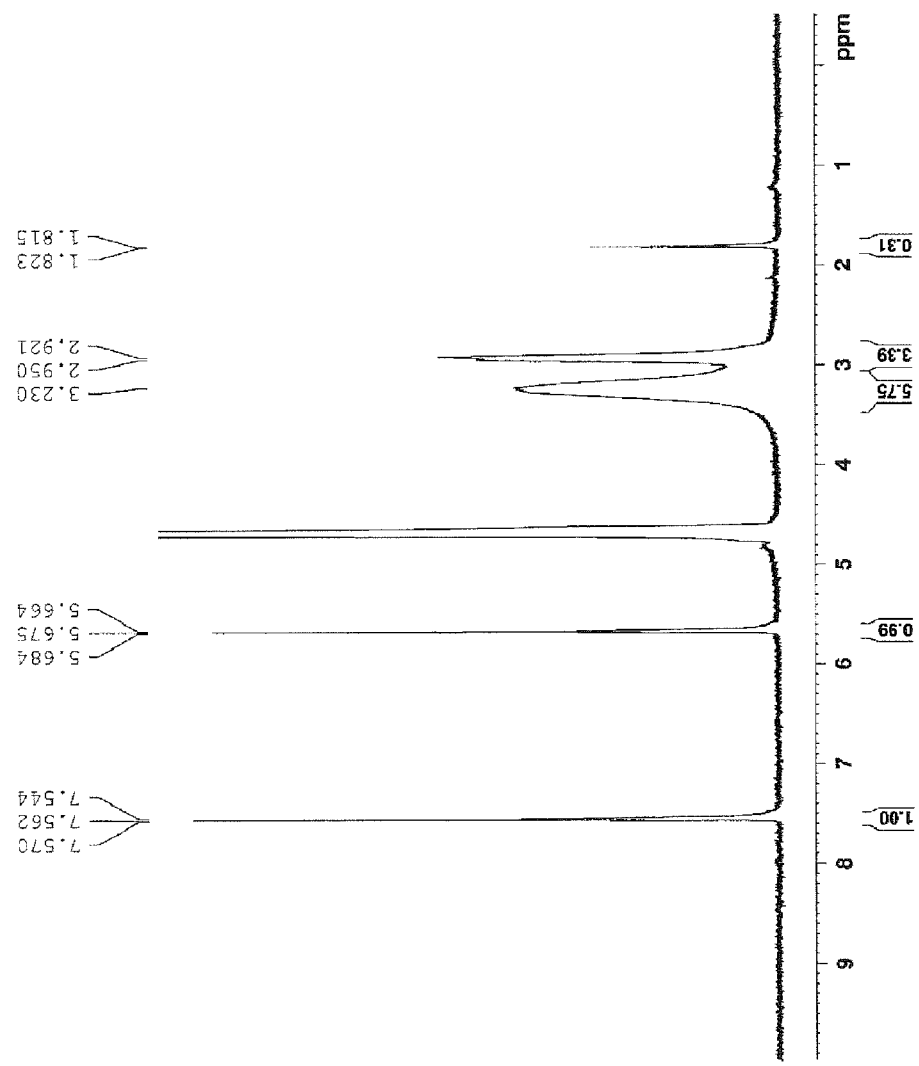
FIG. 20 shows $^1$H-NMR of OB-121.
Figure 21:
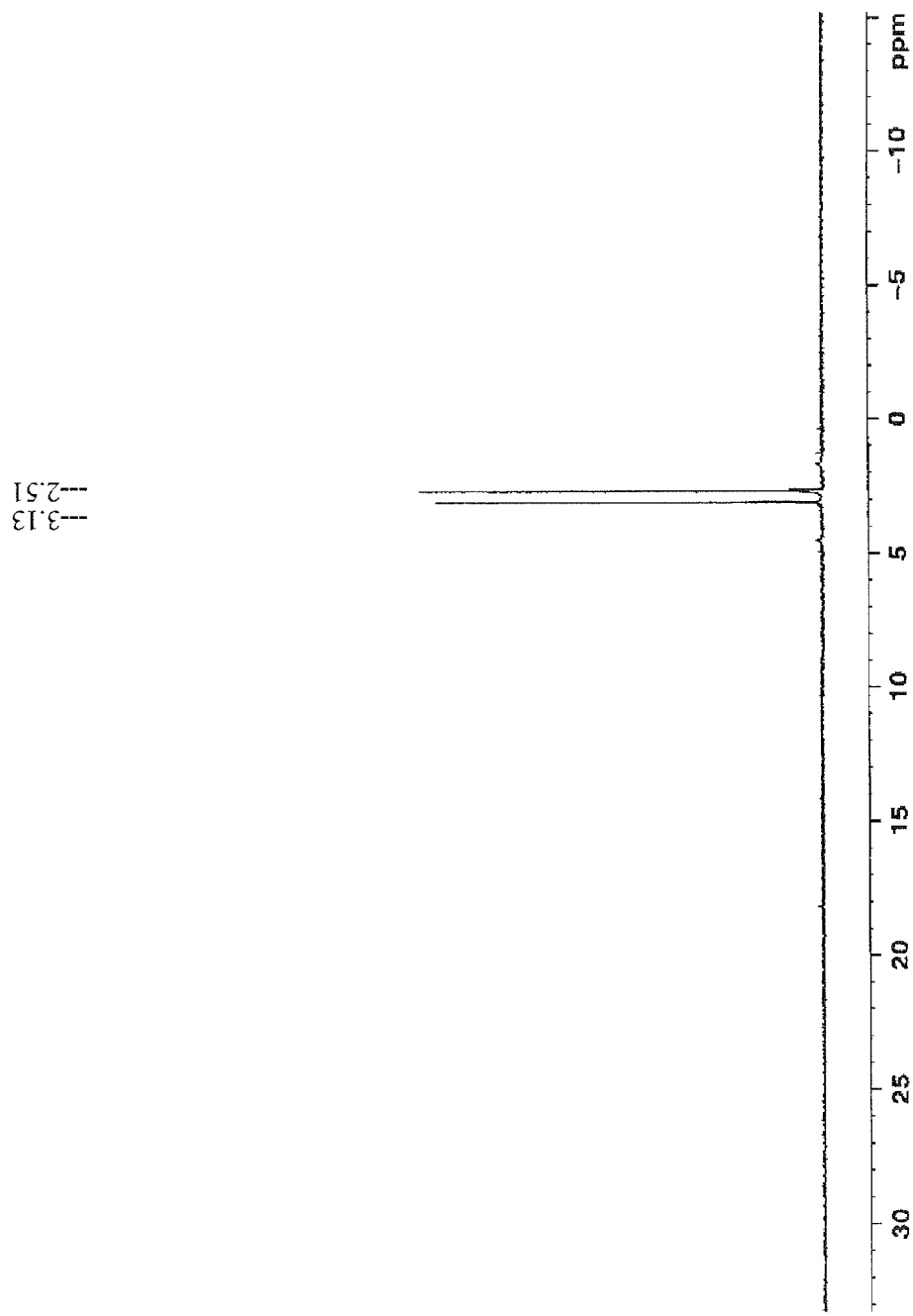
FIG. 21 shows $^{31}$P-NMR of OB-121.

1.3159 g of sodium hydroxide was added to the mixture at room temperature. The pH was around 5 resulting in orange turbid material. Then added more 1.6952 g of sodium hydroxide into the mixture. The orange turbid material turned to brown when the pH reached around 10. The mixture was filtered by 0.45 µM nylon membrane, then the filtrate was dialyzed with a dialysis membrane, wherein the molecular weight cut off (MWCO) of the membrane was less than 500 Daltons. The product was lyophilized and isolated with Sephadex G-75. The structure was confirmed by proton NMR (FIG. 20, δ 7.5; δ 5.6; δ 3.2; δ 2.9; δ 1.8) and $^{31}$P NMR (FIG. 21).

Example 8. Synthesis of 1,4,8,11-Tetraazacyclotetradecane-1,4,8,11-tetrakis(2-hydroxy-ethylenebisphosphonate) (OB-141)

432.5 mg (1.0 mmol) of TETA (1,4,8,11-Tetraazacyclotetradecane-1,4,8,11-tetraacetic acid; MW 432.5) was dissolved in the solution of 1368 µL of 85% phosphorous acid (24 mmol as a 85% phosphorous acid) and 6.7 mL of chlorobenzene in 20 mL 2-neck flask equipped with caustic gas scrubber, reflux condenser, and additional funnel. Then the mixture was pre-heated around 100-110° C. 1745 µL (20 mmol) of trichlorophosphine was added to the hot mixture drop by drop for 15 min to 1 hour.

Then a thick precipitate was formed. After heating the mixture for overnight followed by cooling down it, the bulk of the chlorobenzene was decanted, and the remaining solvent was evaporated under reduced pressure condition. The white or yellow residue was taken up in 10 mL of water and heated to reflux for 1 hour.

Figure 22:
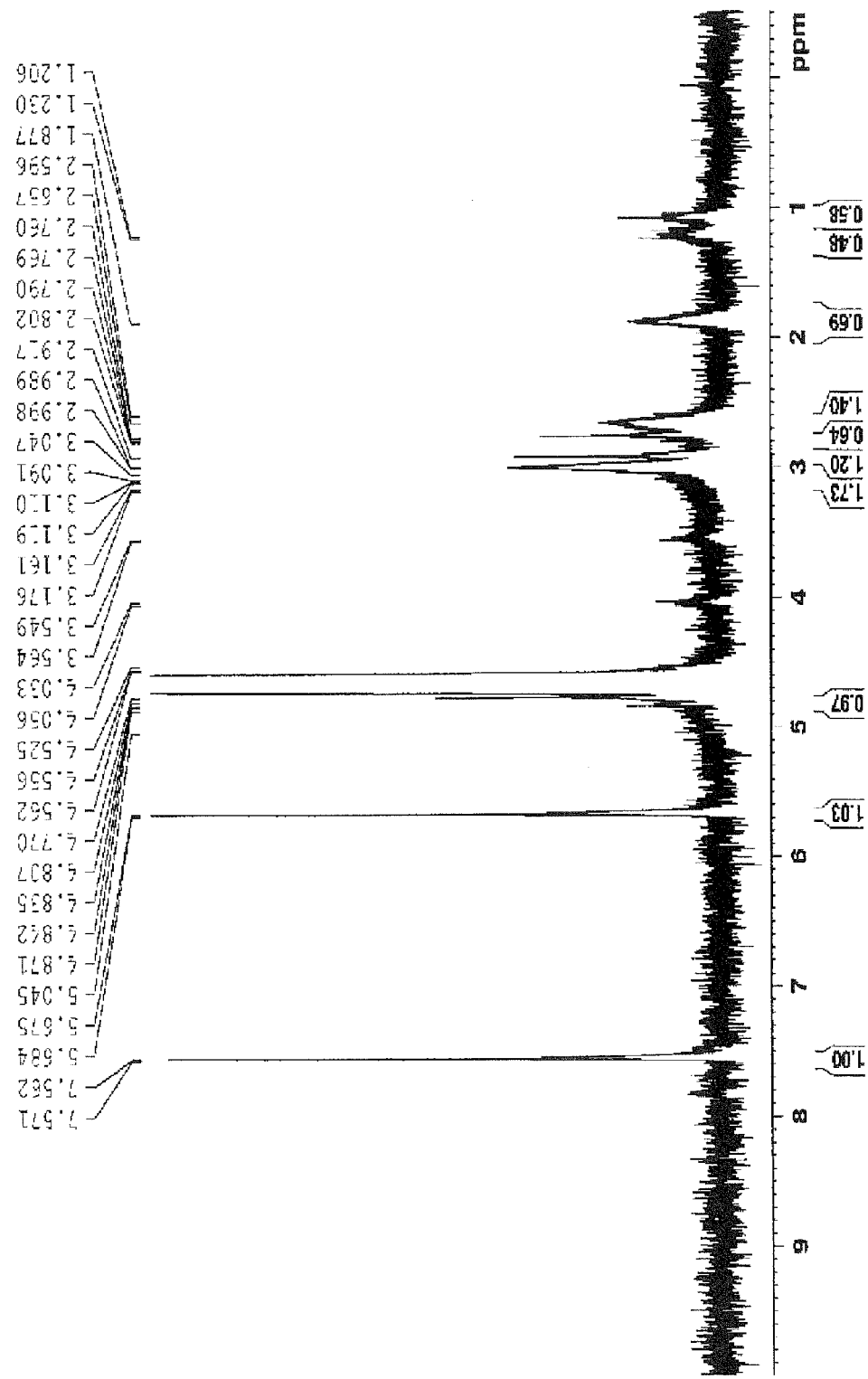
FIG. 22 shows $^1$H-NMR of OB-141.
Figure 23:
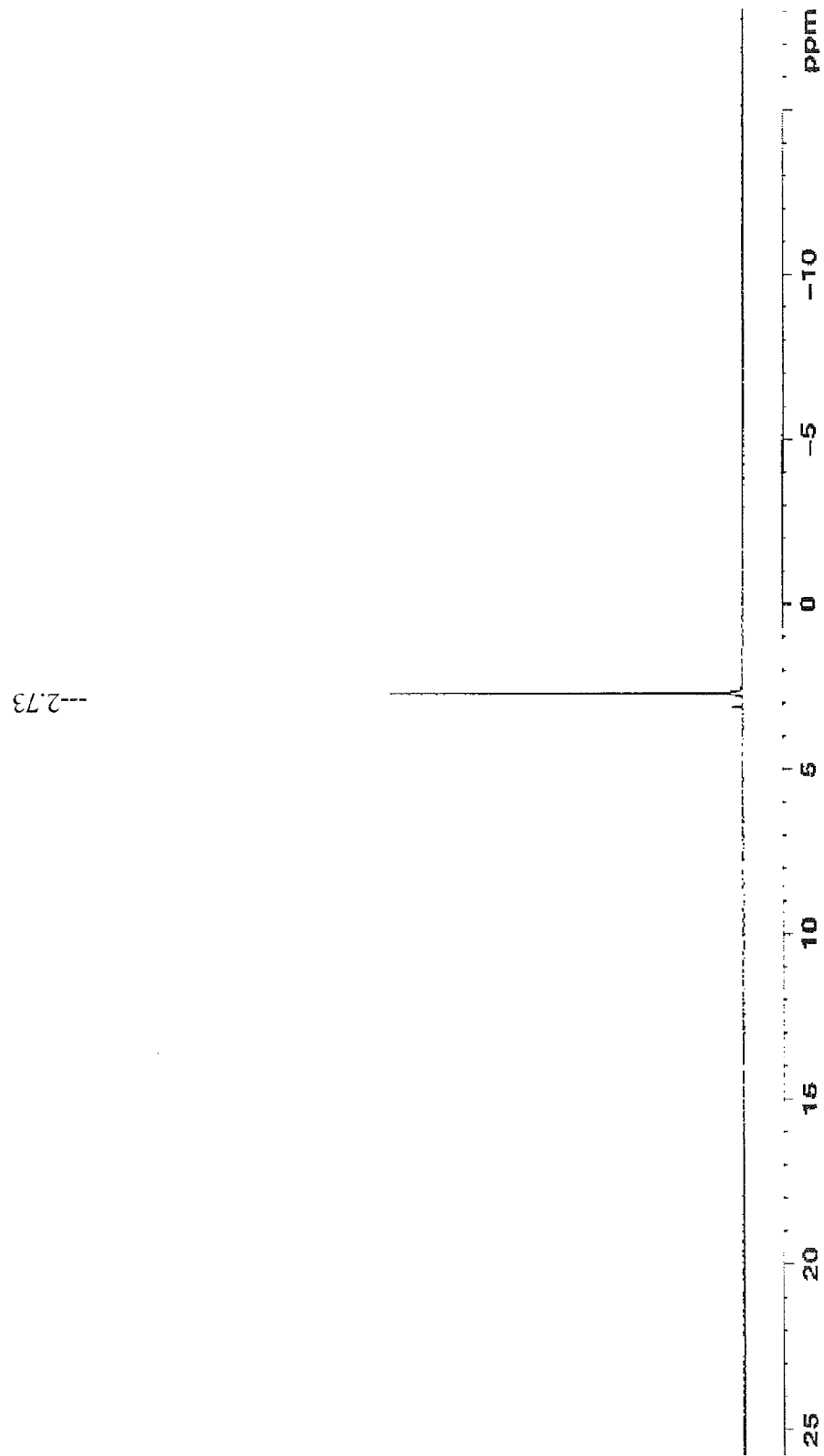
FIG. 23 shows $^{31}$P-NMR of OB-141.

1.3159 g of sodium hydroxide was added to the mixture at room temperature. The pH was adjusted around 5 and an orange turbid material was obtained. Then, further 1.6952 g of sodium hydroxide into the mixture. The orange turbid material turned to brown when pH reached around 10. The mixture was filtered with 0.45 µM nylon membrane, then the filtrate was dialyzed with a dialysis membrane, wherein the molecular weight cut off (MWCO) of the membrane was less than 500 Daltons. The product was lyophilized and isolated with Sephadex G-75. The structure was confirmed by proton NMR (FIG. 22, δ 7.5, singlet; δ 5.6, triplet; δ 4.7, broad multiplet; δ 3.1; δ 1.8; δ 1.2) and $^{31}$P NMR (FIG. 23, δ 2.7).

Example 9. Synthesis of 1,4,7,10-Tetraazacyclododecane-1,4,7,10-tetrakis(3-hydroxy-propylenebisphosphonate) (OB-122)

Step a. Synthesis of 1,4,7,10-Tetraazacyclododecane-1,4,7,10-tetrapropanoic acid ethyl ester The solution of 1722.7 mg (10 mmol) of 1,4,7,10-Tetraazacyclododecane, 324.4 mg of $FeCl_3$ (2 mmol) in 50 mL of acetonitrile and 4348 µL of ethyl acrylate (40 mmol) was mixed and stirred at room temperature. Then low boiling material was evaporated under reduced pressure condition. The residue was isolated by silica-gel column chromatography with gradient solvent system (chloroform:methanol=100:1-10:5) to gain 3.5 g of pale yellow 1,4,7,10-Tetraazacyclododecane-1,4,7,10-tetrapropanoic acid ethyl ester.

Step b. Synthesis of 1,4,7,10-Tetraazacyclododecane-1,4,7,10-tetrapropanoic acid The solution of 2863.7 mg of 1,4,7,10-Tetraazacyclododecane-1,4,7,10-tetrapropanoic acid ethyl ester (5 mmol) in 3 mL of ethyl alcohol was added to 20 mL of 4N sodium hydroxide (80 mmol). The mixture was heated for 1 hour at 60° C. and then low boiling material was evaporated. The residue was isolated with Sephadex-G50 to get 2.250 g of 1,4,7,10-Tetraazacyclododecane-1,4,7,10-tetrapropanoic acid tetra sodium salt.

Step c. Synthesis of 1,4,7,10-Tetraazacyclododecane-1,4,7,10-tetrakis (2-hydroxy-propylenebisphosphonate)

2.193 g of 1,4,7,10-Tetraazacyclododecane-1,4,7,10-tetrapropanoic acid (4 mmol) was dissolved in the solution of 1368 μL of 85% phosphorous acid (24 mmol as a 85% phosphorous acid) and 6.7 mL of chlorobenzene in 20 mL 2-neck flask equipped with caustic gas scrubber, reflux condenser, and additional funnel. Then the mixture was pre-heated around 100-110° C. 1745 μL (20 mmol) of trichlorophosphine was added to the hot mixture drop by drop for 15 min to 1 hour.

Then a thick precipitate was formed. After heating the mixture for overnight followed by cooling down it, the bulk of the chlorobenzene was decanted, and the remaining solvent was evaporated under reduced pressure condition. The white or yellow residue was taken up in 10 mL of water and heated to reflux for 1 hour.

1.3159 g of sodium hydroxide was added to the mixture at room temperature. The pH was adjusted around 5 and an orange turbid material was obtained. Then, further 1.6952 g of sodium hydroxide into the mixture. The orange turbid material turned to brown when pH became 10. The mixture was filtered with 0.45 μM nylon membrane, and then the filtrate was dialyzed with a membrane, wherein the molecular weight cut off (MWCO) of the membrane was less than 500 Daltons. The product was lyophilized and isolated with Sephadex G-75 to get 1149 mg of 1,4,7,10-Tetraazacyclododecane-1,4,7,10-tetrakis(2-hydroxy-propylenebisphosphonate).

Figure 24:
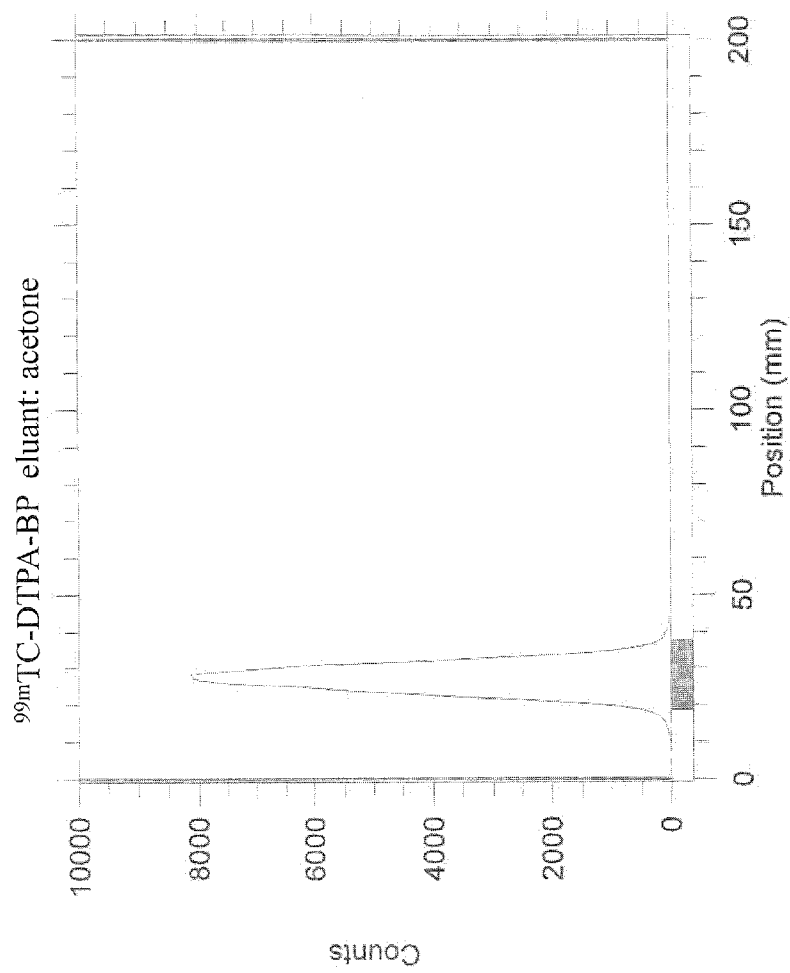
FIGS. 24-25 show Radio-TLC Analysis of $^{99m}$Tc-DTPA-BP.
Figure 25:
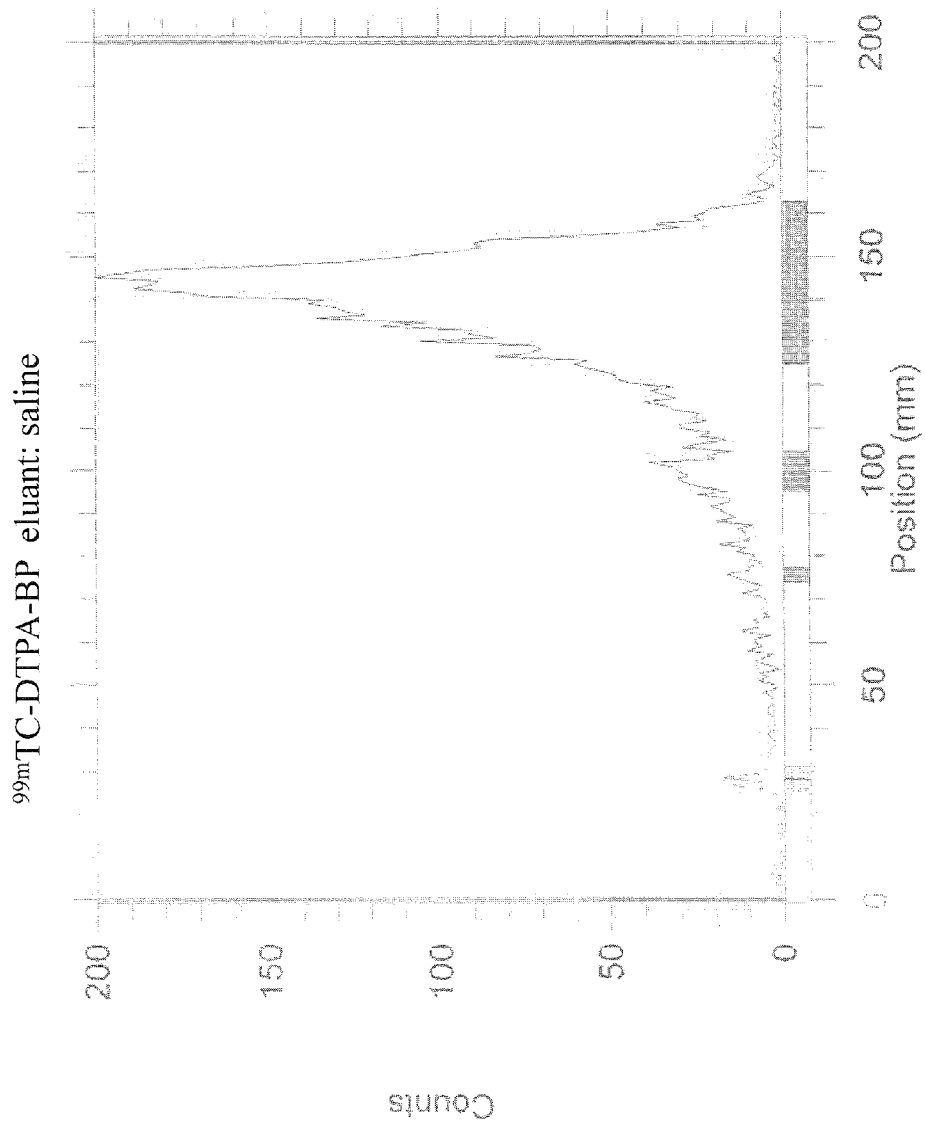

Test 1: General Radiolabeling Procedure of Chelator-Based Bone Seeking Agents with $^{99m}$Tc 5 mg of the compound of present disclosure (ex: OB-121) was dissolved in 0.2 ml of water, then added tin chloride (0.1 mg in 0.1 ml of water) in at room temperature. Afterward, sodium pertechnetate (5 mCi) was added into the aforesaid solution. The procedure of labeling $^{68}$Ga was similar to labeling $^{99m}$Tc except tin chloride was not added. Then the radiochemical purity of the compound of present disclosure was determined by TLC (ITLC SG, Gelman Sciences, Ann Arbor, Mich.). The results of $^{99m}$Tc-DTPA-BP and $^{68}$Ga-MAMA-AMDP under different conditions are shown in FIG. 24-27 (the experimental conditions are described in the following tables 1-4). According to radio-TLC (Bioscan, Washington, D.C.) analysis, only one peak shows in FIG. 24, 25, 26 and the radiochemistry purity of these peak was 100%, which means that $^{99m}$Tc or $^{68}$Ga were stable conjugated with the compounds of present disclosure. Moreover, no matter using acetone or saline as the dispersion phase, the radiochemistry purity would not be affected by the polarity of the dispersion phase, as shown in FIG. 24 and FIG. 25. When the dispersion phase was changed from acetone to saline, the peak position changed, but the radiochemistry purity was not. Further, FIG. 28 shows the effect of physical amount on the labeling $^{68}$Ga efficiency of DTPA-AMDP DTPA-BP and DTPA. As shown in FIG. 28, the radiochemical purity increases while the amount of DTPA-AMDP DTPA-BP or DTPA increases. When the concentration of the three compounds are same, the radiochemical purity is the highest when using DTPA-BP, which means DTPA-BP has better labeling efficiency than DTPA.

TABLE 1

Experimental Conditions of FIG. 24
Method: QuickStart
File: 070220-1557.R001

| Comments |
|---|
| 99mTc-DTPA-BP, acetone, 15 cm |

Analysis Parameters

| | | | |
|---|---|---|---|
| Bkg Subtraction: | none | Origin: | 0.0 mm |
| Normalization: | none | Front: | 200.0 mm |
| Total Counts: | 86764.0 (43382.0 CPM) | Region: | 0.0-200.0 mm |
| Total File Counts: | 86772 | | |

Region Analysis

| | | | |
|---|---|---|---|
| Definition: | Peak Search | | |
| Peak Slope: | 2.0 counts/mm | | |
| Min Width: | 2.3 mm | | |
| Min pct of Total | 0.0% | | |

| Reg | (mm) Start | (mm) Stop | (mm) Centroid | RF | Region Counts | Region CPM | % of Total | % of ROI |
|---|---|---|---|---|---|---|---|---|
| Rgn 1 | 18.9 | 37.6 | 27.5 | 0.137 | 84748.0 | 42373.0 | 97.67 | 100.00 |
| 1 Peaks | | | | | 84748.0 | 42373.0 | 97.67 | 100.00 |

TABLE 2

Experimental Conditions of FIG. 25
Method: QuickStart
File: 070220-1547.R001

| Comments |
|---|
| 99mTC-DTPA-BP, Saline, 16 cm |

Analysis Parameters

| | | | |
|---|---|---|---|
| Bkg Subtraction: | none | Origin: | 0.0 mm |

TABLE 2-continued

| | | | |
|---|---|---|---|
| Normalization: | none | Front: | 200.0 mm |
| Total Counts: | 6168.0 (3081.5 CPM) | Region: | 0.0-200.0 mm |
| Total File Counts: | 6168 | | |

Region Analysis

| | |
|---|---|
| Definition: | Peak Search |
| Peak Slope: | 2.0 count/mm |
| Min Width: | 2.3 mm |
| Min pct of Total | 0.0% |

| Reg | (mm) Start | (mm) Stop | (mm) Centroid | RF | Region Counts | Region CPM | % of Total | % of ROI |
|---|---|---|---|---|---|---|---|---|
| Rgn 1 | 25.1 | 31.3 | 27.9 | 0.140 | 82.0 | 31.0 | 1.01 | 1.30 |
| Rgn 2 | 74.0 | 77.6 | 75.4 | 0.377 | 48.0 | 24.5 | 0.80 | 1.03 |
| Rgn 3 | 95.4 | 104.3 | 99.6 | 0.498 | 268.0 | 134.0 | 4.35 | 6.63 |
| Rgn 4 | 124.8 | 163.0 | 141.8 | 0.709 | 4380.0 | 2190.0 | 71.07 | 92.04 |
| 4 Peaks | | | | | 4758.0 | 2379.5 | 77.22 | 100.00 |

TABLE 3

Figure 26:
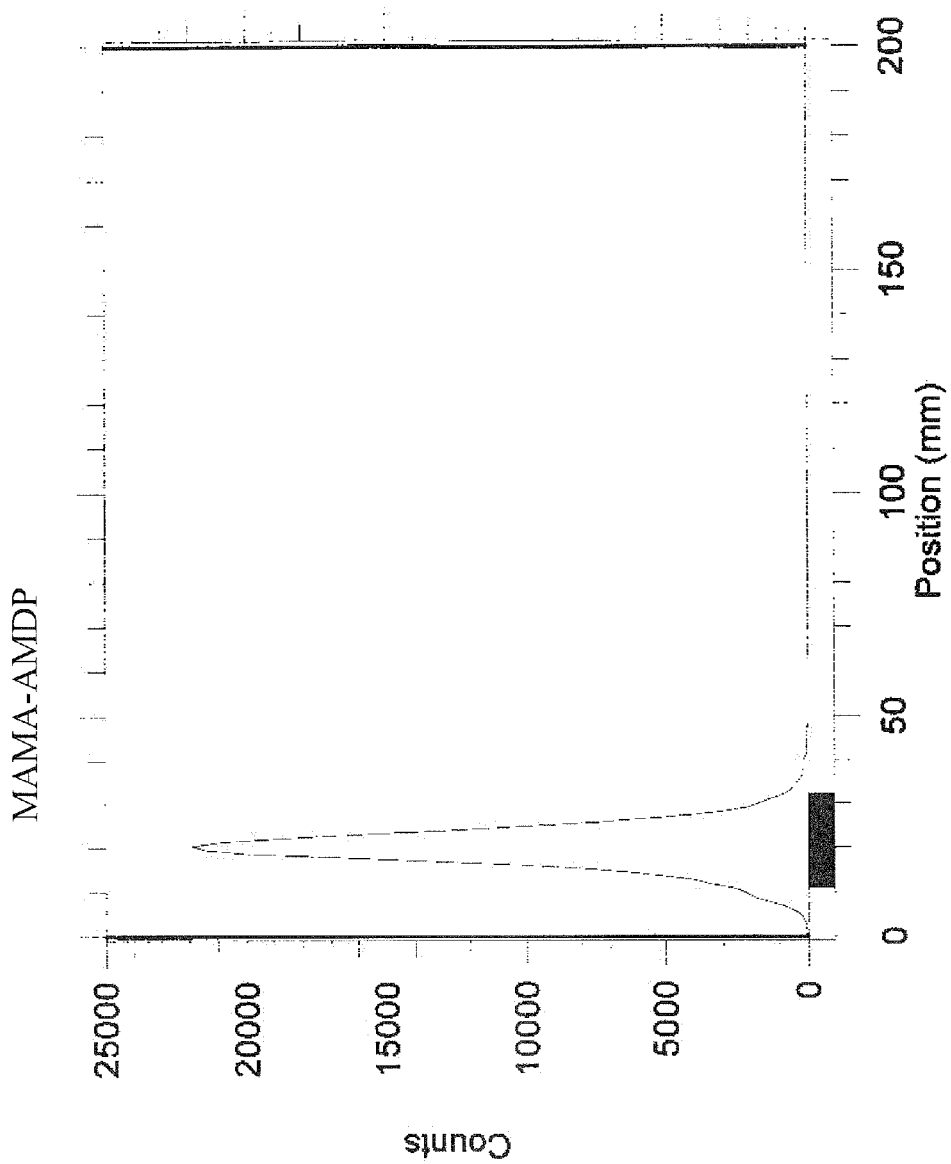
FIGS. 26-27 show Radio-TLC Analysis of $^{68}$Ga-MAMA-AMDP.

Experimental Conditions of FIG. 26
Method: QuickStart
File: 070516-1720.R001

Comments

MAMA-AMDP(0 mM)10 minheat

Analysis Parameters

| | | | |
|---|---|---|---|
| Bkg Subtraction: | none | Origin: | 0.0 mm |
| Normalization: | none | Front: | 200.0 mm |
| Total Counts: | 248344.0 (124172.0 CPM) | Region: | 0.0-200.0 mm |
| Total File Counts: | 248481 | | |

Region Analysis

| | |
|---|---|
| Definition: | Peak Search |
| Peak Slope: | 2.0 counts/mm |
| Min Width: | 2.3 mm |
| Min pct of Total: | 0.0% |

| Reg | (mm) Start | (mm) Stop | (mm) Centroid | RF | Region Counts | Region CPM | % of Total | % of ROI |
|---|---|---|---|---|---|---|---|---|
| Rgn 1 | 10.9 | 32.2 | 20.5 | 0.103 | 235638.0 | 117819.0 | 94.88 | 100.00 |
| 1 Peaks | | | | | 235638.0 | 117819.0 | 94.88 | 100.00 |

TABLE 4

Figure 27:
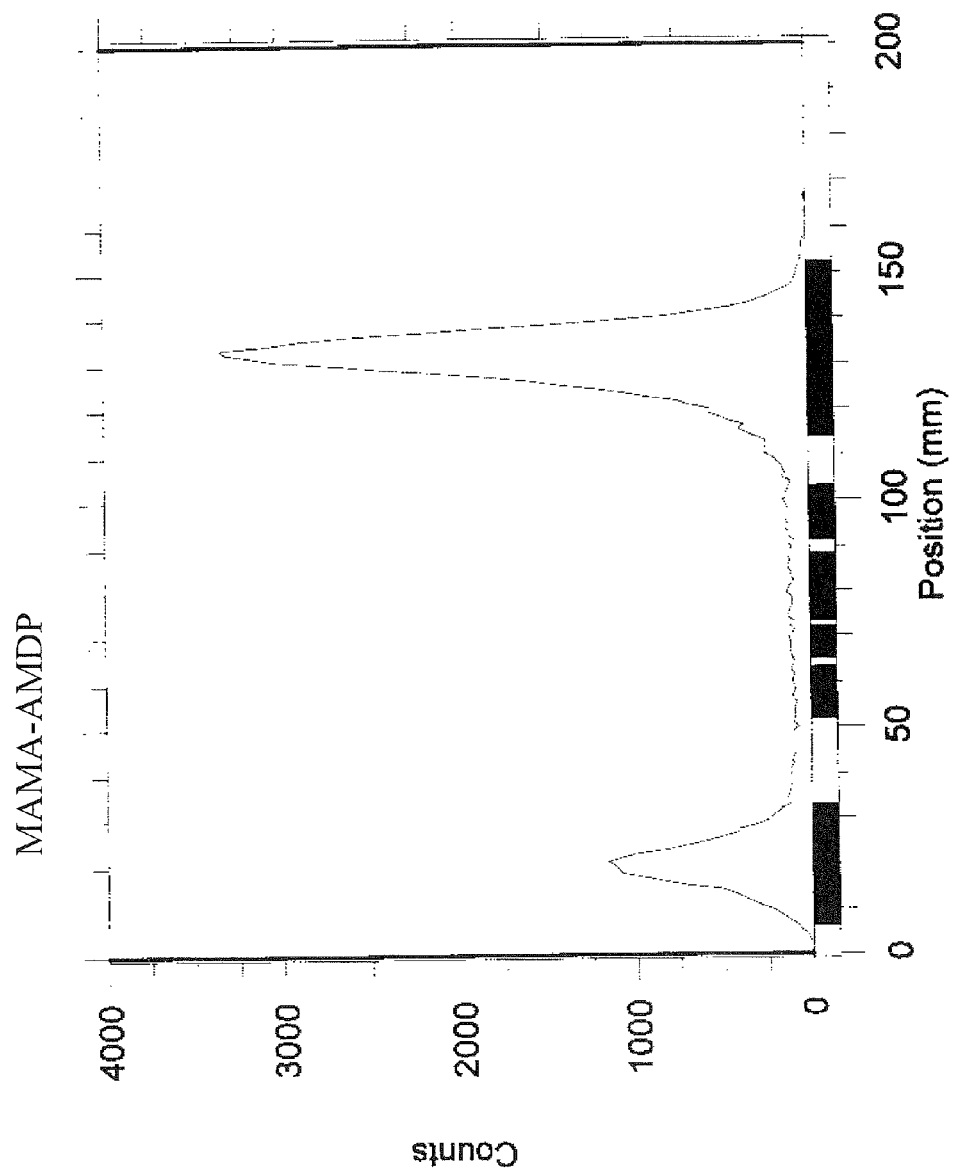
Figure 28:
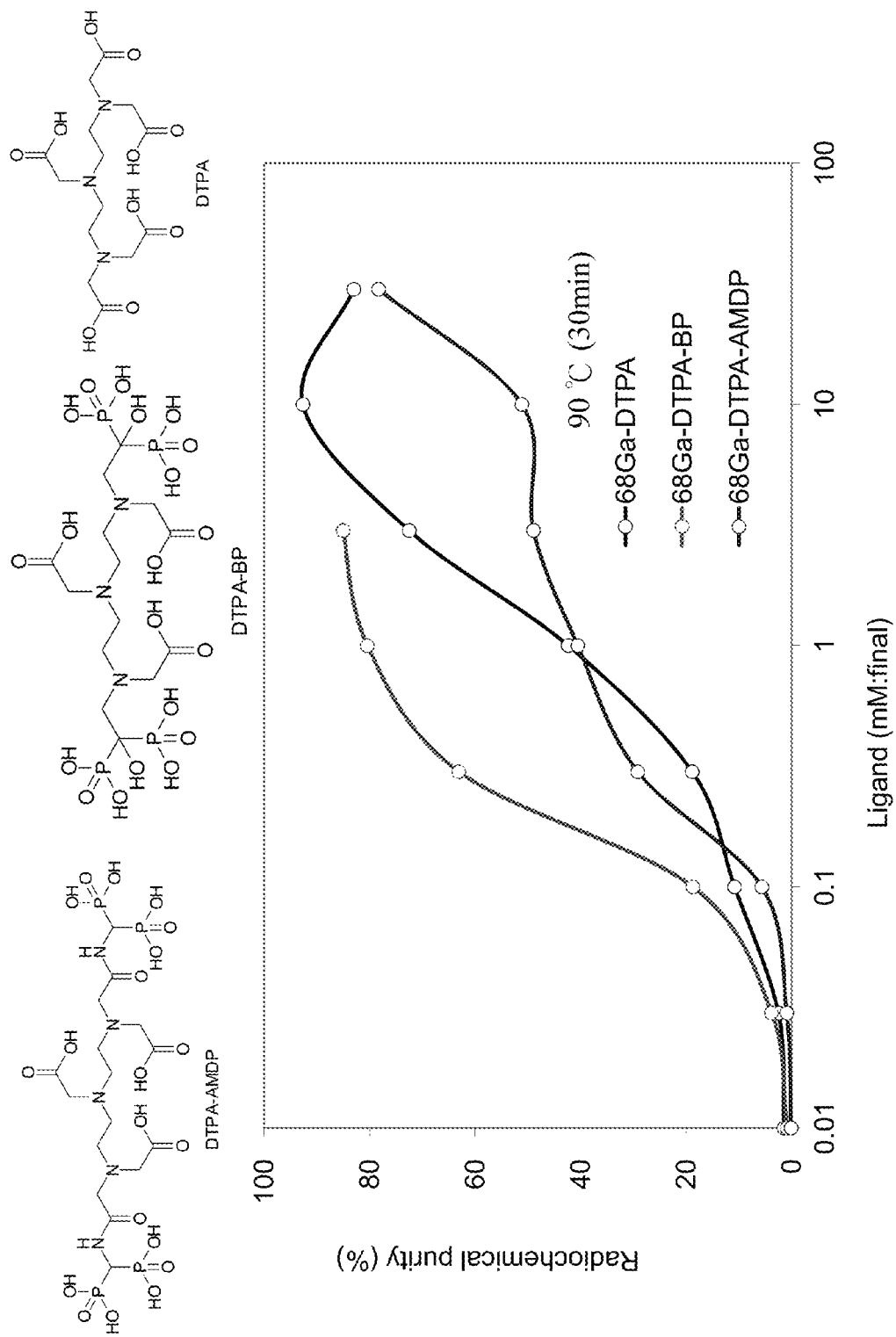
FIG. 28 show physical amount on the labeling efficiency.

Experimental Conditions of FIG. 27
Method: QuickStart
File: 070516-1812.R001

Comments

| | | | |
|---|---|---|---|
| MAMA-AMDP (10 mM) 60 minRT | | | |
| Bkg Subtraction: | none | Origin: | 0.0 mm |
| Normalization: | none | Front: | 200.0 mm |
| Total Counts: | 78984.0 (78984.0 CPM) | Region: | 0.0-200.0 mm |
| Total File Counts: | 79000 | | |

Region Analysis

| | |
|---|---|
| Definition: | Table |

| Reg | (mm) Start | (mm) Stop | (mm) Centroid | RF | Region Counts | Region CPM | % of Total | % of ROI |
|---|---|---|---|---|---|---|---|---|
| Rgn 1 | 6.4 | 33.1 | 19.9 | 0.100 | 16331.0 | 16331.0 | 20.68 | 22.25 |

TABLE 4-continued

| Rgn 2 | 51.8 | 63.4 | 57.3 | 0.287 | 1248.0 | 1248.0 | 1.58 | 1.70 |
| --- | --- | --- | --- | --- | --- | --- | --- | --- |
| Rgn 3 | 65.1 | 72.3 | 68.2 | 0.341 | 874.0 | 874.0 | 1.11 | 1.19 |
| Rgn 4 | 73.2 | 77.6 | 75.0 | 0.375 | 549.0 | 549.0 | 0.70 | 0.75 |
| Rgn 5 | 77.6 | 82.9 | 79.8 | 0.399 | 671.0 | 671.0 | 0.85 | 0.91 |
| Rgn 6 | 82.9 | 88.3 | 85.2 | 0.426 | 697.0 | 697.0 | 0.88 | 0.95 |
| Rgn 7 | 90.9 | 103.4 | 96.9 | 0.485 | 1805.0 | 1805.0 | 2.29 | 2.46 |
| Rgn 8 | 114.1 | 152.3 | 131.5 | 0.658 | 51235.0 | 51235.0 | 64.87 | 69.79 |
| 8 Peaks | | | | | 73410.0 | 73410.0 | 92.94 | 100.00 |

Test 2. Scintigraphic Imaging Studies

Figure 29:
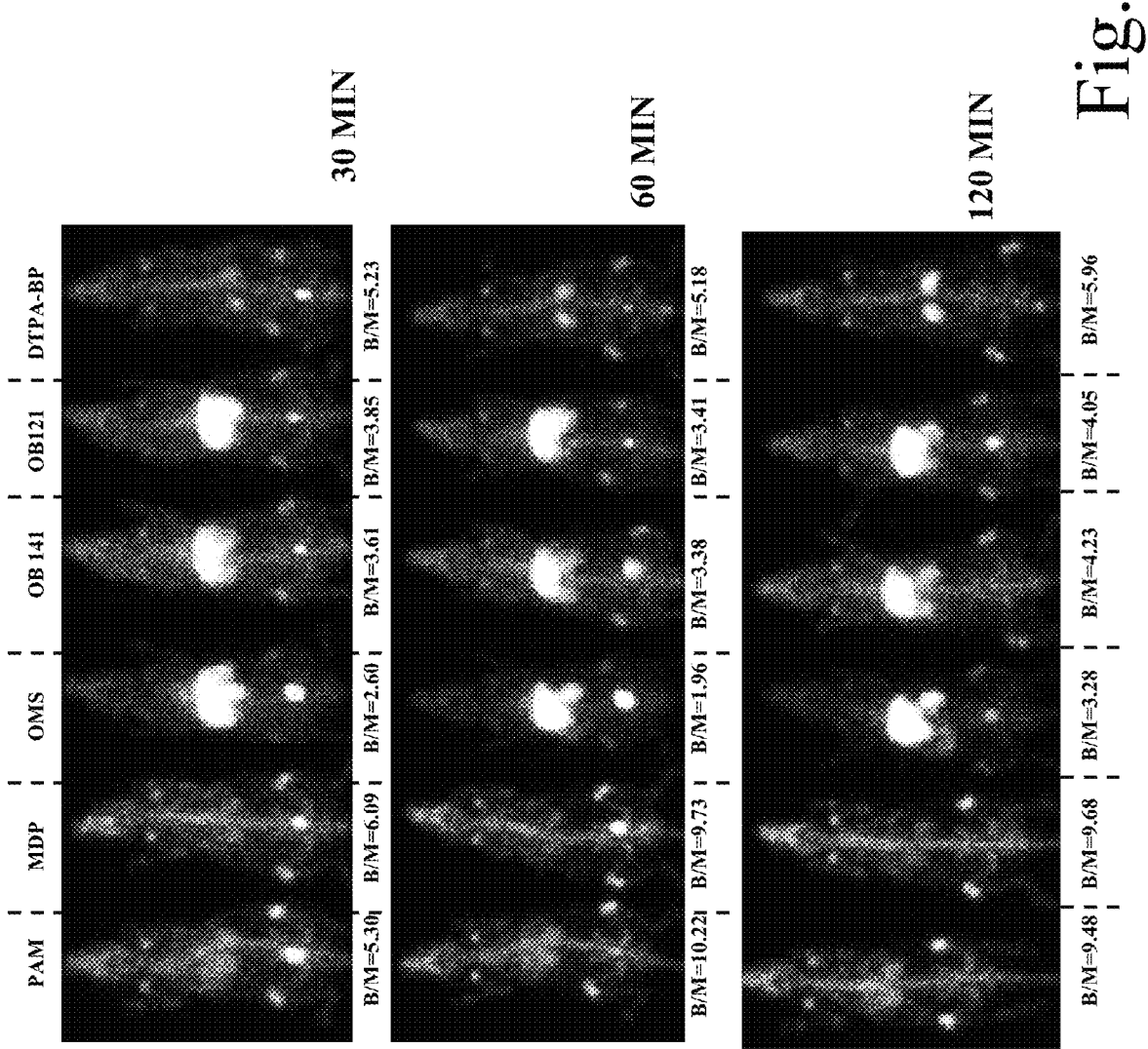
FIG. 29 is a planar scintigraphy of $^{99m}$Tc-Compounds (300 mCi/rat, iv, at 30-120 min acquired 500,000, count) in normal rats. The numbers are Bone/Muscle count density ratios (counts/pixel).
Figure 30:
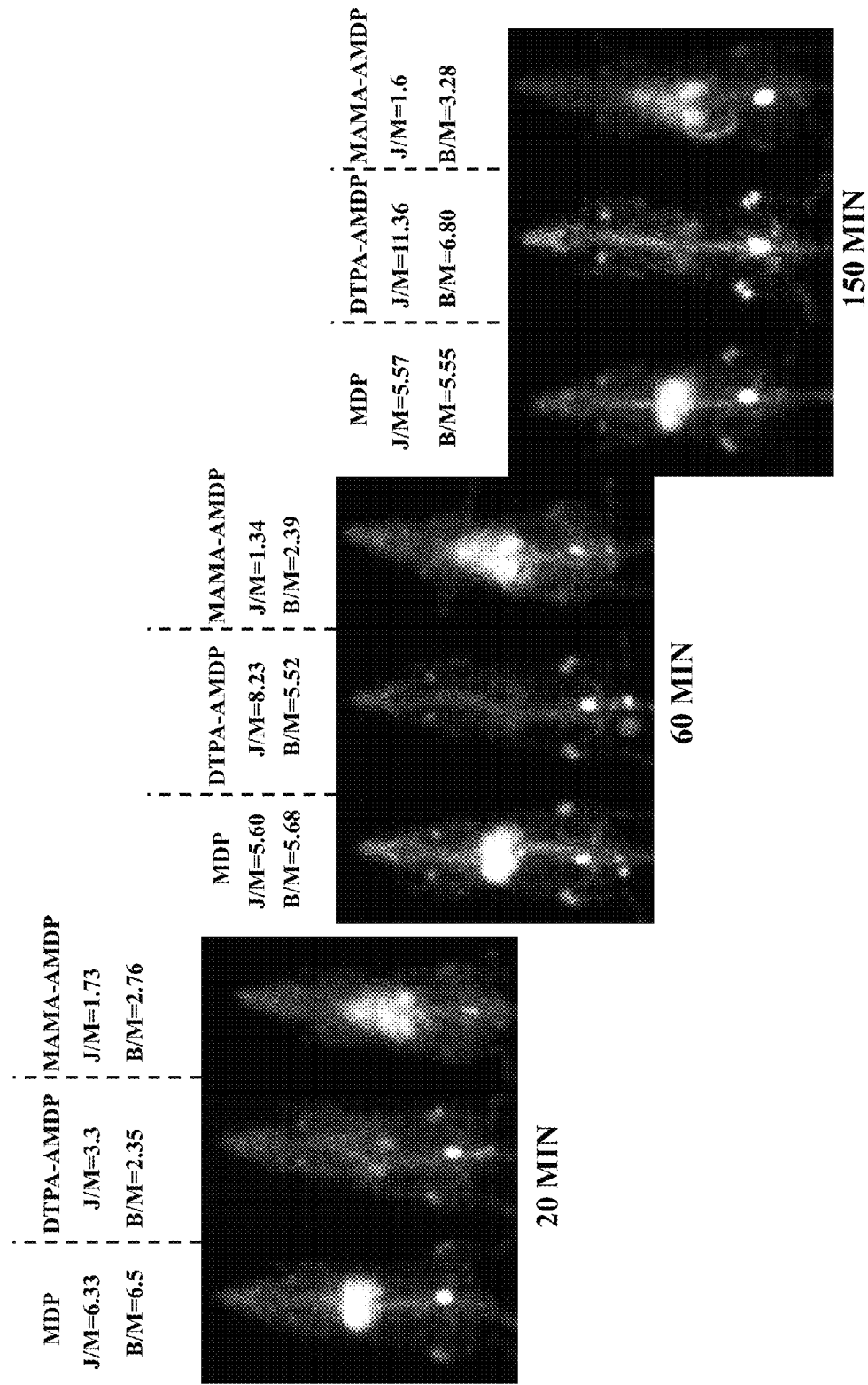
FIG. 30 is a planar scintigraphy of $^{99m}$Tc-Compounds (300 mCi/rat, iv, at 30-150 min acquired 500,000, count) in normal rats. The numbers are Joint/Muscle and vertebral bone/Muscle count density ratios (counts/pixel).
Figure 31:
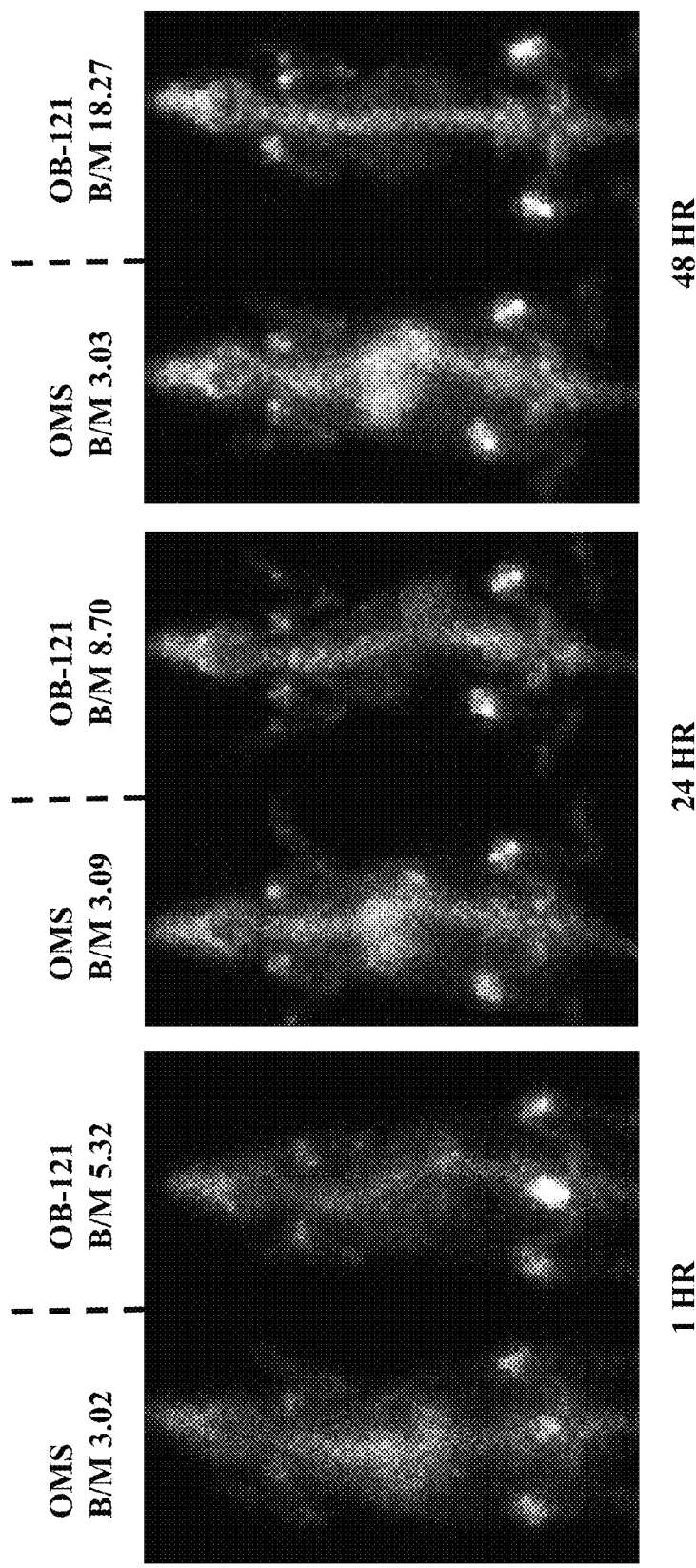
FIG. 31 is planar scintigraphy of $^{111}$In-Compounds (450 mCi/rat, iv, at 1-48 hours acquired 500,000, count) in normal rats. The numbers are Bone/Muscle count density ratios (counts/pixel) to demonstrate superior bone uptake in In-OMS and In-OB121 compounds.

To demonstrate whether the compounds of present disclosure could image bones, groups of normal female Fischer 344 rats were administered with 300 µCi of $^{99m}$Tc-PAM, $^{99m}$Tc-MDP, $^{99m}$Tc-OMS, $^{99m}$Tc-OB141, $^{99m}$Tc-OB121, $^{99m}$Tc-DTPA-BP, $^{99m}$Tc-DTPA-AMDP, and $^{99m}$Tc-MAMA-AMDP. Pamidronate (PAM), Methyl diphosphonate (MDP) and OMS are bone-related agents and were used as control group in present invention. Scintigraphic images, captured by a gamma camera equipped with low-energy, parallel-hole collimator or micro-PET, were obtained in 0.5-2 hours. The selected images are shown in FIGS. 29 and 30, wherein FIG. 29 compares the planar images of 30, 60, and 120 min of normal rats which were taken $^{99m}$Tc-PAM, $^{99m}$Tc-MDP, $^{99m}$Tc-OMS, $^{99m}$Tc-OB141, $^{99m}$Tc-OB 121 and $^{99m}$Tc-DTPA-BP respectively. FIG. 30 compares the planar images of 20, 60, and 150 min of normal rats which were taken $^{99m}$Tc-MDP, $^{99m}$Tc-DTPA-AMDP, and $^{99m}$Tc-MAMA-AMDP respectively. Higher joint-to-muscle (J/M) or bone-to-muscle (B/M) ratios and the better quality of bone images were achieved. All compounds of present invention were more stable and had higher and more rapid uptake in the skeleton with pronounced lesion-to-normal bone activity ratios than PAM MDP or OMS and DTPA-chelator so that showed better labeling yield and images quality in normal healthy F-344 rats. Besides, as tetraazacyclic groups are very lipophilic so that they may have potential applications in the treatment of osteoporosis. Thus, tetraazacyclic groups were labeled with In-111 for longer observation. FIG. 31 shows planar images of normal rats after $^{111}$In-OMS or $^{111}$In-OB121 had been administrated 1, 24, and 48 hours. The images showed that OB-121 is a better compound for getting high quality images.

Figure 32:
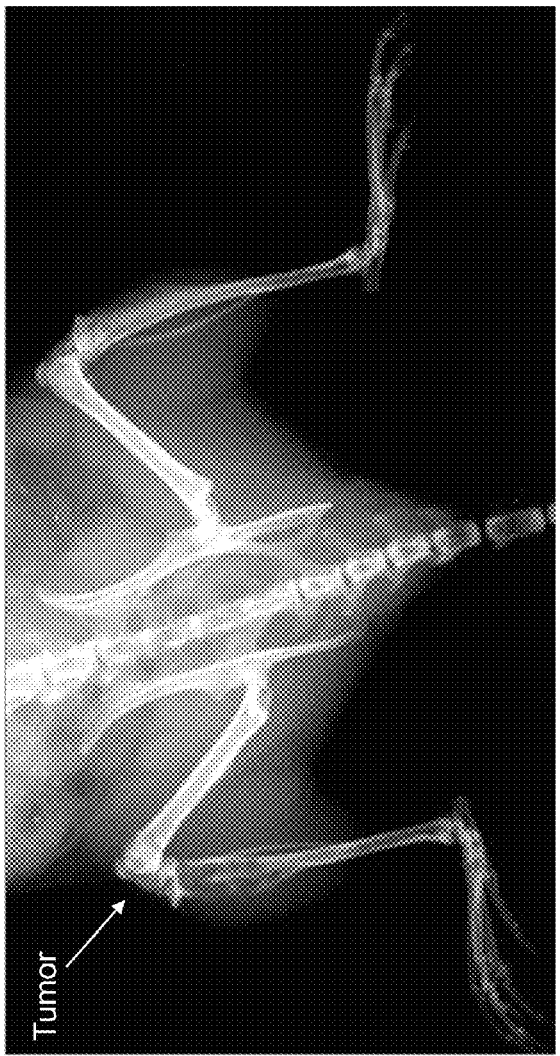
FIG. 32 shows X-rays image of legs of the tested mice after injecting tumor cells for 3 weeks (Osteolytic model).
Figure 33:
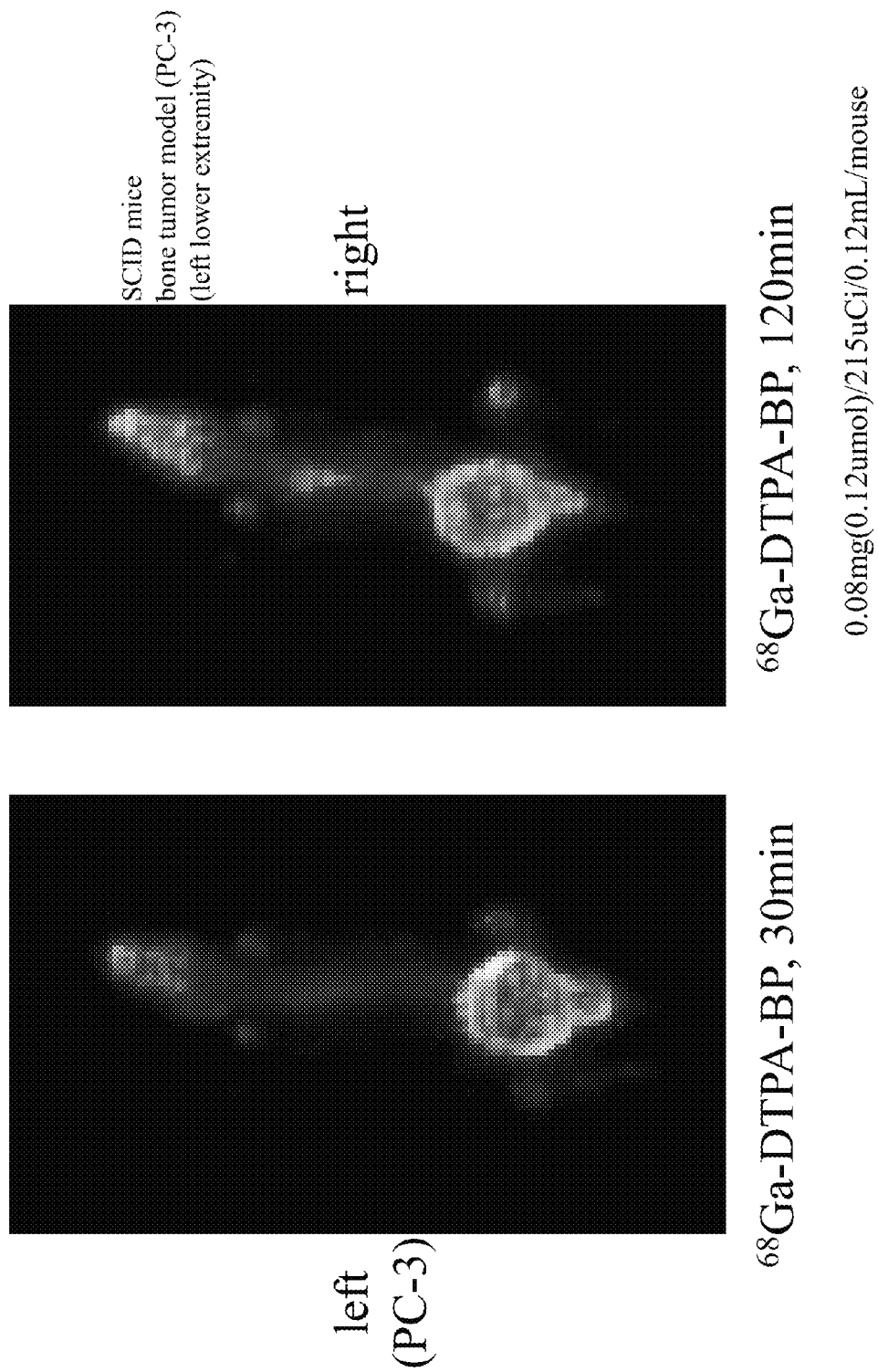
FIG. 33 is MicroPET Images of $^{68}$Ga-DTPA-BP.
Figure 34:
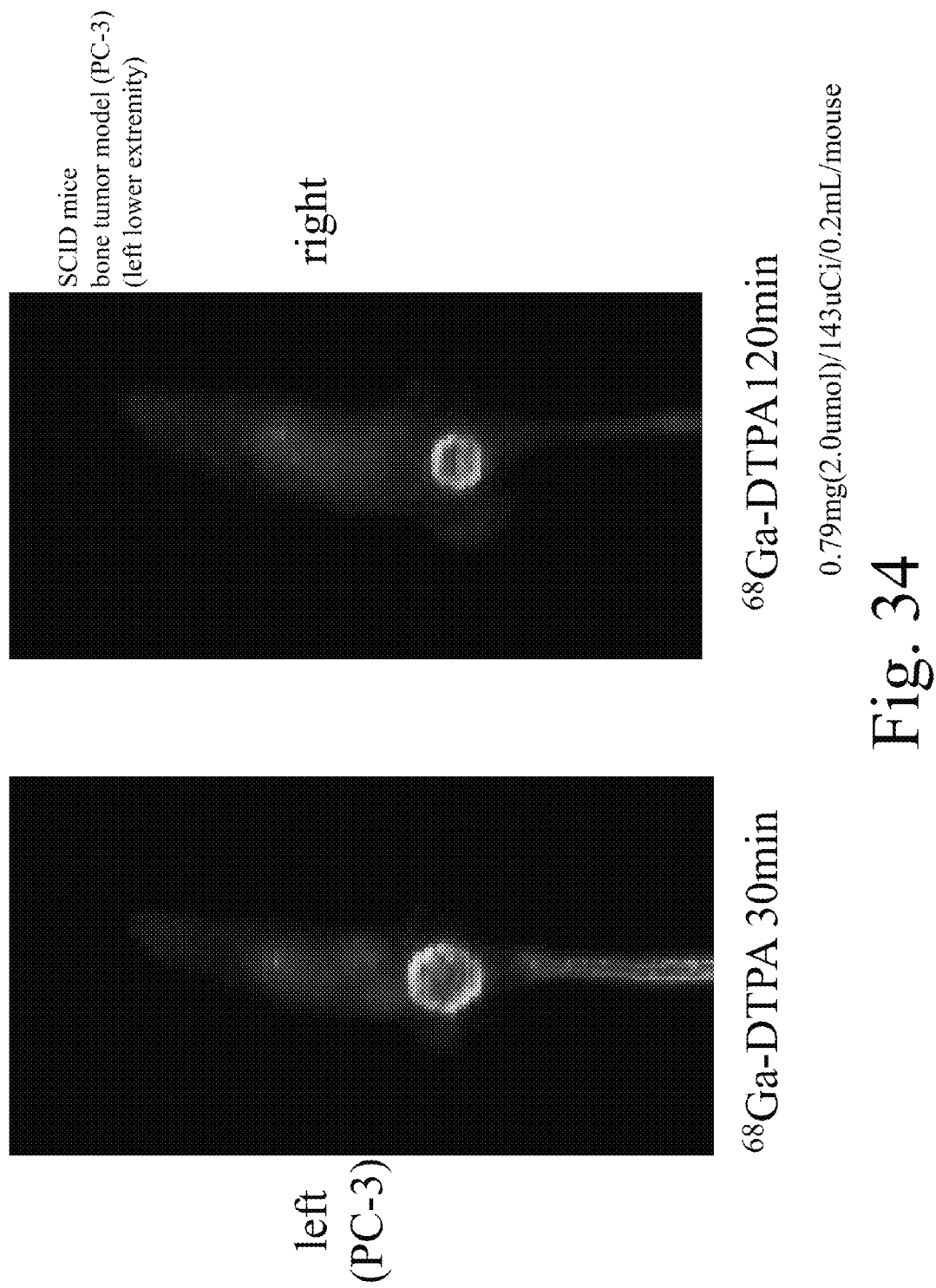
FIG. 34 is MicroPET Images of $^{68}$Ga-DTPA.

The conventional procedure to create animal model with osteoporosis is to remove ovaries of the experimental animals. However, this model creates diffused osteoporosis. To ascertain whether DTPA-BP is a good candidate for imaging of bone osteolytic effects, prostate tumor cells (PC-3) were injected into left tibia bone of a SCID mouse and fetal bovine serum (FBS) was injected into right tibia bone of the same SCID mouse for comparison. After 3 weeks, the lesions could be assessed by x-ray as well as by PET $^{68}$Ga-DTPA-BP, but not $^{68}$Ga-DTPA, as shown in FIGS. 32-34.

In summary, all of the compounds of the present invention can be used for providing good bone scanning images, and the best candidate of $^{68}$Ga-bisphosphonate determined from our animal studies was $^{68}$Ga-DTPA-BP because it imaging quality. These analogues may have potential application in therapy. The physical amount used for imaging was 0.1 mg. It may be enough to produce the quality of images.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A bone seeking agent of the following formula:

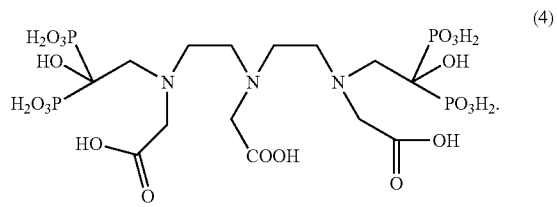

(4)

2. The bone seeking agent of claim 1, wherein the agent is chelated with a metal.

3. The bone seeking agent of claim 2, wherein the metal is Tc-99m, Ga-67, Ga-68, In-111, Cu (61, 62, 64), Gd, Fe or a combination thereof.

4. A method of scanning bones, which comprises administering to an animal containing bones an imaging amount of the bone seeking agent of claim 1 and imaging the bones with imaging technology for bone metastasis and/or osteoporosis.

5. The method of claim 4, wherein the imaging technology is CT, MRI, PET or SPECT.

* * * * *